United States Patent
Hofmann et al.

(10) Patent No.: US 8,759,060 B2
(45) Date of Patent: Jun. 24, 2014

(54) PEG-MODIFIED ARGININE/LYSINE OXIDOREDUCTASE

(71) Applicant: APIT Laboratories GmbH, Potsdam (DE)

(72) Inventors: Christian J. Hofmann, Berlin (DE); Michael Lindemann, Berlin (DE)

(73) Assignee: Thomas Rudel, Berlin (DE)

( * ) Notice: Subject to any disclaimer, the term of this patent is extended or adjusted under 35 U.S.C. 154(b) by 0 days.

(21) Appl. No.: 14/021,492

(22) Filed: Sep. 9, 2013

(65) Prior Publication Data

US 2013/0344052 A1     Dec. 26, 2013

Related U.S. Application Data

(63) Continuation of application No. 12/667,920, filed as application No. PCT/EP2007/004587 on May 23, 2007, now abandoned.

(30) Foreign Application Priority Data

May 26, 2006 (EP) .................................. 06010824

(51) Int. Cl.

| | | |
|---|---|---|
| *C12N 9/02* | (2006.01) | |
| *G01N 1/30* | (2006.01) | |
| *A61K 38/43* | (2006.01) | |
| *A61K 47/48* | (2006.01) | |
| *C12N 9/96* | (2006.01) | |
| *C12N 9/06* | (2006.01) | |

(52) U.S. Cl.
CPC ........ *C12N 9/0022* (2013.01); *A61K 47/48215* (2013.01); *C12N 9/96* (2013.01)
USPC .......................... 435/189; 424/94.1; 435/40.5

(58) Field of Classification Search
CPC ......... C12N 9/0022; C12N 9/96; A61K 38/44
USPC .................................. 435/189, 40.5; 424/94.1
See application file for complete search history.

(56) References Cited

FOREIGN PATENT DOCUMENTS

| | | |
|---|---|---|
| EP | 0 898 968 A1 | 3/1999 |
| EP | WO 2004/065415 A2 | 8/2004 |
| JP | 2003 292457 A | 10/2003 |

OTHER PUBLICATIONS

International Preliminary Examination Report for International Application No. PCT/EP2007/004587, Nov. 27, 2008.
International Search Report for International Application No. PCT/EP2007/004587, Dec. 6, 2007.
Fang Jun, et al., "Tumor-targeted delivery of polyethylene glycol-conjugated D-amino acid oxidase for antitumor therapy via enzymatic generation of hydrogen peroxide," Cancer Research, vol. 62, No. 11, Jun. 1, 2002, pp. 3138-3143.
Sawa, T, et al., "Tumor-targeting chemotherapy by a xanthine oxidase-polymer conjugate that generates oxygen-free radicals in tumor tissue," Cancer Research, vol. 60, No. 3, Feb. 1, 2000, pp. 666-671.
Butzke, D. et al., "Cloning and biochemical characterization of APIT, a new l-amino acid oxidase from *Aplysia punctata*," Toxicon, Elmsford, NY, vol. 46, No. 5, Oct. 2005, pp. 479-489.
Lukasheva, E.V., et al., "L-lysine alpha-oxidase: Physicochemical and biological properties," Biochemistry (Moscow), vol. 67, No. 10, Oct. 2002, pp. 1394-1402.
Butzke, D. et al., "Hydrogen Peroxide Produced by *Aplysia* Ink Toxin Kills Tumor Cells Independent of Apoptosis Via Peroxiredoxin I Sensitive Pathways," Cell Death and Differentiation, Edward Arnold, Oxford, GB, vol. 11, No. 6, Jun. 2004, pp. 608-617.
Jung S K, Mai A, Iwamoto M, Arizono N, Fujimoto D, Sakamaki K, Yonehara S, 2000, J Immunol. 165, 1491-1497.
Du, X. Y. & Clemetson, K J, 2002, Snake venom L-amino acid oxidases. Toxicon, 40, pp. 659-665.
Ponnudurai G., ChungMC, Tan NH, 1994, Arch Biochem. Biophys 313, pp. 373-378.
Ehara T., Kitajima S, Kanzawa N, Tamiya T, Tsuchiya T, 2002, FEBS Lett 531, pp. 509-512.
Branden et al. (Introduction to Protein Structure, Garland Publishing Inc., New York, p. 247, 1991).
Brenda Database. EC 1.4.3.3. Retrived from the internet on Jul. 19, 2012 via http://www.brendaenzymes.info/php/result_flat.php4?ecno=1.4.3.3.
Guo et al.Proc Natl Acad Sci USA. Jun. 22, 2004;101 (25):9205-10.
Roberts et al. Chemistry for peptide and protein PEGylation. Adv Drug Deliv Rev. Jun. 17, 2002;54(4):459-76. Review.
Veronese et al. PEGylation, successful approach to drug delivery. Drug Discov Today. Nov. 1, 2005:10(21):1451-8. Review.

*Primary Examiner* — Yong Pak
(74) *Attorney, Agent, or Firm* — Michael Fedrick; Loza & Loza, LLP

(57) ABSTRACT

The present invention is directed to an arginine/lysine oxidoreductase modified with polyethylene glycol, a production method thereof, and methods of treating disorders responsive to a modification of amino acid levels reactive oxygen species and/or ammonium.

11 Claims, 13 Drawing Sheets

Figure 1

Figure 2:
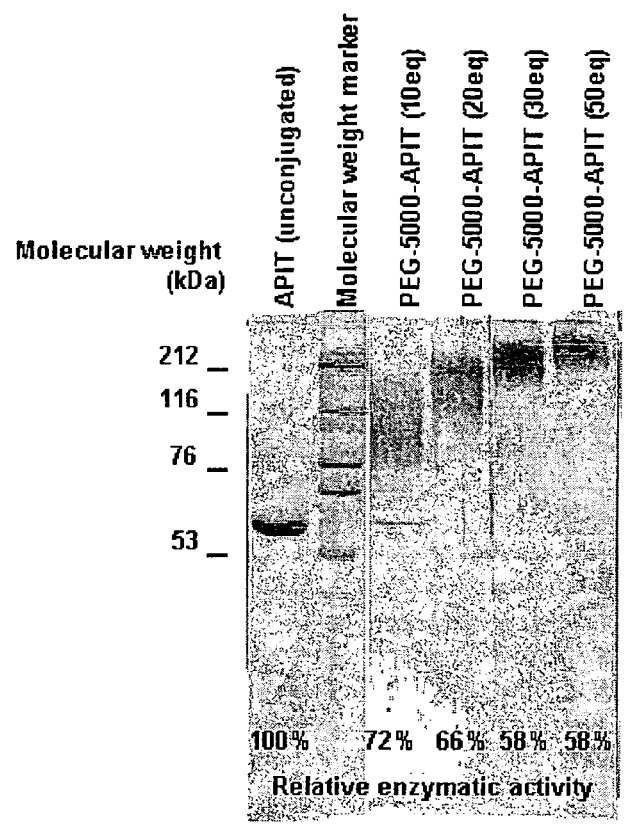

Primary amino acid sequence of Arginine/Lysine-oxidoreductase, APIT (Seq ID NO:8)

```
  1   MDGVSRNRRQ CNREVCGSTY DVAVVGAGPG GANSAYMLRD SGLDIAVFEY SDRVGGRLFT
 61   YQLPNTPDVN LEIGGMRFIE GAMHRLWRVI SELGLTPKVF KEGFGKEGRQ RFYLRGQSLT
121   KKQVKSGDVP YDLSPEEKEN QGNLVEYYLE KLTGLQLNGE PLKREVALKL TVPDGRFLYD
181   LSFDEAMDLV ASPEGKEFTR DTHVFTGEVT LDASAVSLFD DHLGEDYYGS EIYTLKEGLS
241   SVPQGLLQAF LDAADSNEFY PNSHLKALRR KTNGQYVLYF EPTTSKDGQT TINYLEPLQV
301   VCAQRVILAM PVYALNQLDW NQLRNDRATQ AYAAVRPIPA SKVFMTFDQP WWLENERKSW
361   VTKSDALFSQ MYDWQKSEAS GDYILIASYA DGLKAQYLRE LKNQGEDIPG SDPGYNQVTE
421   PLKDTILDHL TEAYGVERDS IPEPVTAASQ FWTDYPFGCG WITWRAGFHF DDVISTMRRP
481   SLKDEVYVVG ADYSWGLISS WIEGALETSE NVINDYFL
```

Nucleotide sequence SEQ ID NO:7 encoding SEQ ID NO:8

```
ATGGACGGTGTCAGCAGAAACAGACGTCAATGTAACAGAGAGGTGTGCGGTTCTACCTACGATG
TGGCCGTCGTGGGGGCGGGGCCTGGGGGAGCTAACTCCGCCTACATGCTGAGGGACTCCGGCCT
GGACATCGCTGTGTTCGAGTACTCAGACCGAGTGGGCGGCCGGCTGTTCACCTACCAGCTGCCC
AACACACCCGACGTTAACCTGGAGATTGGAGGCATGAGGTTCATCGAAGGCGCCATGCACAGGC
TCTGGAGGGTCATTTCAGAACTCGGCCTAACCCCCAAGGTGTTCAAGGAAGGTTTCGGCAAGGA
GGGCAGACAAAGATTCTACCTGCGGGGACAGAGCCTGACCAAGAAACAGGTCAAGAGTGGGGAC
GTACCCTATGACCTCAGCCCGGAGGAGAAAGAAAACCAGGGAAATCTGGTCGAATACTACCTGG
AGAAACTGACAGGTCTACAACTCAACGGCGAGCCGCTCAAACGTGAGGTTGCGCTTAAACTAAC
CGTGCCGGACGGCAGATTCCTCTATGACCTCTCGTTTGACGAAGCCATGGATCTGGTTGCCTCC
CCTGAGGGCAAAGAGTTCACCCGAGACACGCACGTCTTCACAGGAGAGGTCACCCTGGACGCGT
CGGCTGTCTCCCTCTTCGACGACCACCTGGGAGAGGACTACTATGGCAGTGAGATCTACACCCT
AAAGGAAGGACTGTCTTCCGTCCCACAAGGGCTCCTACAGGCTTTTCTGGACGCCGCAGACTCC
AACGAGTTCTATCCCAACAGCCACCTGAAGGCCCTGAGACGTAAGACCAACGGTCAGTATGTTC
TTTACTTTGAGCCCACCACCTCCAAGGATGGACAAACCACAATCAACTATCTGGAACCCCTGCA
GGTTGTGTGTGCACAGAGAGTCATCCTGGCCATGCCGGTATACGCTCTGAACCAACTAGACTGG
AATCAGCTCAGAAATGACCGAGCCACCCAAGCGTACGCTGCCGTTCGCCCGATTCCTGCAAGTA
AGGTGTTCATGACCTTTGATCAGCCCTGGTGGTTGGAGAACGAGAGGAAATCCTGGGTCACCAA
GTCGGACGCGCTTTTCAGCCAAATGTACGACTGGCAGAAGTCTGAGGCGTCCGGAGACTACATC
CTGATCGCCAGCTACGCCGACGGCCTCAAAGCCCAGTACCTGCGGGAGCTGAAGAATCAGGGAG
AGGACATCCCAGGCTCTGACCCAGGCTACAACCAGGTCACCGAACCCCTCAAGGACACCATTCT
TGACCACCTCACTGAGGCTTATGGCGTGGAACGAGACTCGATCCCGGAACCCGTGACCGCCGCT
TCCCAGTTCTGGACAGACTACCCGTTTGGCTGTGGATGGATCACCTGGAGGGCCGGCTTCCATT
TCGATGACGTCATCAGCACCATGCGTCGCCCGTCACTGAAAGATGAGGTATACGTGGTGGGAGC
CGACTACTCCTGGGGACTTATCTCCTCCTGGATAGAGGGCGCTCTTGAGACCTCGGAAAACGTC
ATCAACGACTACTTCCTC
```

Pegylation of Arginine/Lysine-oxidoreductase, APIT with PEG-5000

Activity of PEG-5000-APIT in the presence of anti-APIT polyclonal antibodies

Effect of single intravenous dose of APIT (250U/kg) and APIT (1000 U/kg) on Plasma-Lysine levels in mice Effect of single intravenous dose of APIT (250U/kg) and APIT (1000 U/kg) on Plasma-Arginine levels in mice Comparison of single intravenous dose of APIT (250U/kg) and PEG-5000-APIT at an equivalent dose of 250 U/kg on Plasma-Lysine levels in mice Comparison of single intravenous dose of APIT (250U/kg) and PEG-5000-APIT at an equivalent dose of 250 U/kg on Plasma-Arginine levels in mice Administration Dose-dependent depletion of Plasma-Lysine levels after single intravenous administration of PEG-5000-APIT to mice Dose-dependent depletion of Plasma-Arginine levels after single intravenous administration of PEG-5000-APIT to mice Antitumor efficacy of PEG-5000-APIT

Figure 11

```
    M   S   S   A   V   L   L   A   C   A   L   V   I   S   V   H   A   D   G   IV  C
ATGTCGTCTGCTGTGCTTCTCCTGGCTTGTGCGTTGGTCATCTCTGTCCACGCCGACGGTATCTGC
...TCGTCTGCTGTGCTTCTCCTGGCTTGTGCGTTGGTCATCTCTGTCCACGCCGACGGTGTCTGC
..................................................GACGGTATCTGC

R   N   R   R   Q   C   N   R   E   V   C   G   S   T   Y   D   V   A   V   V   G   A
AGAAACAGACGTCAATGTAACAGAGAGGTGTGCGGTTCTACCTACGATGTGGCCGTCGTGGGGGCG
AGAAACAGACGTCAATGTAACAGAGAGGTGTGCGGTTCTACCTACGATGTGGCCGTCGTGGGGGCG
AGAAACAGACGTCAATGTAACAGAGAGGTGTGCGGTTCTACCTACGATGTGGCTGTCGTGGGGGCG

G   P   G   G   A   N   S   A   Y   M   L   R   D   S   G   L   D   I   A   V   F   E
GGGCCTGGGGGAGCTAACTCCGCCTACATGCTGAGGGACTCCGGCCTGGACATCGCTGTGTTCGAG
GGGCCTGGGGGAGCTAACTCCGCCTACATGCTGAGGGACTCCGGCCTGGACATCGCTGTGTTCGAG
GGGCCTGGGGGAGCTAACTCCGCCTACATGCTGAGGGACTCCGGCCTGGACATCGCTGTGTTCGAG

Y   S   D   R   V   G   G   R   L   F   T   Y   Q   L   P   N   T   P   D   V   N   L
TACTCGGACCGAGTGGGCGGCCGGCTGTTCACCTACCAGCTGCCCAACACACCCGACGTTAACCTG
TACTCAGACCGAGTGGGCGGCCGGCTGTTCACCTACCAGCTGCCCAACACACCCGACGTTAATCTC
TACTCAGACCGAGTGGGCGGCCGGCTGTTCACCTACCAGCTGCCCAACACACCCGACGTTAATCTC

E   I   G   G   M   R   F   I   E   G   A   M   H   R   L   W   R   V   I   S   E   L
GAGATTGGCGGCATGAGGTTCATCGAAGGCGCCATGCACAGGCTCTGGAGGGTCATTTCAGAACTC
GAGATTGGCGGCATGAGGTTCATCGAGGGCGCCATGCACAGGCTCTGGAGGGTCATTTCAGAACTC
GAGATTGGCGGCATGAGGTTCATCGAGGGCGCCATGCACAGGCTCTGGAGGGTCATTTCAGAACTC

G   L   T   P   K   V   F   K   E   G   F   G   K   E   G   R   Q   R   F   Y   L   R
GGCCTAACCCCCAAGGTGTTCAAGGAAGGTTTCGGCAAGGAGGGCAGACAAAGATTTTACCTGCGG
GGCCTAACCCCCAAGGTGTTCAAGGAAGGTTTCGGAAAGGAGGGCAGACAGAGATTTTACCTGCGG
GGCCTAACCCCCAAGGTGTTCAAGGAAGGTTTCGGAAAGGAGGGCAGACAGAGATTTTACCTGCGG

G   Q   S   L   T   K   K   Q   V   K   S   G   D   V   P   Y   D   L   S   P   E   E
GGACAGAGCCTGACCAAGAAACAGGTCAAGAGTGGGGACGTACCCTATGACCTCAGCCCGGAGGAG
GGACAGAGCCTGACCAAGAAACAGGTCAAGAGTGGGGACGTACCCTATGACCTCAGCCCGGAGGAG
GGACAGAGCCTGACCAAGAAACAGGTCAAGAGTGGGGACGTACCCTATGACCTCAGCCCGGAGGAG

K   E   N   Q   G   N   L   V   E   Y   Y   L   E   K   L   T   G   L   QK  L   N   G
AAAGAAAACCAGGGAAATCTGGTCGAATACTACCTGGAGAAACTGACAGGTCTACAACTCAACGGC
AAAGAAAACCAGGGAAATCTGGTCGAATACTACCTGGAGAAACTGACAGGTCTACAACTCAATGGT
AAAGAAAACCAGGGAAATCTGGTCGAATACTACCTGGAGAAACTGACAGGTCTAAACTCAACGGC

EG  P   L   K   R   E   V   A   L   K   L   T   V   P   D   G   R   F   L   Y   D   L
GAGCCGCTCAAACGTGAGGTTGCGCTTAAACTAACCGTGCCGGACGGCAGATTCCTCTATGACCTC
GAACCGCTCAAACGTGAGGTTGCGCTTAAACTAACCGTGCCGGACGGCAGATTCCTCTATGACCTC
GGACCGCTCAAACGTGAGGTTGCGCTTAAACTAACCGTGCCGGACGGCAGATTCCTCTATGACCTC

S   F   D   E   A   M   D   L   V   A   S   P   E   G   K   E   F   T   R   D   T   H
TCGTTTGACGAAGCCATGGATCTGGTTGCCTCCCCTGAGGGCAAAGAGTTCACCCGAGACACGCAC
TCGTTTGACGAAGCCATGGATCTGGTTGCCTCCCCTGAGGGCAAAGAGTTCACCCGAGACACGCAC
TCGTTTGACGAAGCCATGGACCTGGTTGCCTCCCCTGAGGGCAAAGAGTTCACCCGAGACACGCAC
```

Figure 11 (continued)

```
        V   F   T   G   E   V   T   L  [DG] A   S   A   V   S   L   F   D   D   H   L   G   E
GTCTTCAC[A]GGAGAGGTCACCCTGGACGCGTCGGCTGTCTCCCTCTTCGACGACCACCTGGGAGAG
GTCTTCACCGGAGAGGTCACCCTGG[G]CGCGTCGGCTGTCTCCCTCTTCGACGACCACCTGGGAGAG
GTGTTCACCGGAGA[A]GTCACCCTGGACGCGTCGGCTGTCTCCCTCTTCGACGACCACCTGGGAGAG

D   Y   Y   G   S   E   I   Y   T   L   K   E   G   L   S   S   V   P   Q   G   L   L
GACTACTATGGCAGTGAGATCTACACCCTAAAGGAAGGACTGTCTTCCGTCCCACAAGGGCTCCTA
GACTACTA[C]GGCAGTGAGATCTACACCCT[C]AAGGAAGGACTGTCTTCCGTCCC[T]CAAGGGCTCCTA
GACTACTATGGCAGTGAGATCTACACCCTAAAGGAAGGACTGTCTTCCGTCCCACAAGGGCTCCTA

Q  [AT] F   L   D   A   A   D   S   N   E   F   Y   P   N   S   H   L   K   A   L   R
CAGGCTTTTCTGGACGCCGCAGACTCCAACGAGTTCTATCCCAACAGCCACCTGAAGGCCCTGAGA
CAGGCTTTTCTGGACGCCGCAGACTCCAACGAGTTCTATCCCAACAGCCACCTGAAGGCCCTGAGA
CAG[A]CTTTTCTGGACGCCGCAGACTCCAACGAGTTCTATCCCAACAGCCACCTGAAGGCCCTGAGA

R   K   T   N   G   Q   Y   V   L   Y   F   E   P   T   T   S   K   D   G   Q   T   T
CGTAAGACCAACGGTCAGTATGTTCTTTACTTTGAGCCCACCACCTCCAAGGATGGACAAACCACA
CGTAAGACCAACGGTCAGTATGTTCTTTACTTTGAGCCCACCACCTCCAAGGATGGACAAACCACA
CGTAAGACCAACGGTCAGTATGTTCTTTACTTTGAGCCCACCACCTCCAAGGATGGACAAACCACA

I   N   Y   L   E   P   L   Q   V   V   C   A   Q   R   V   I   L   A   M   P   V   Y
ATCAACTATCTGGAACCCCTGCAGGTTGTGTGTGCACA[A]AGAGTCATCCTGGCCATGCCGGT[A]TAC
ATCAACTATCTGGAACCCCTGCAGGTTGTGTGTGCACAGAGAGTCAT[T]CTGGCCATGCCGGTCTAC
ATCAACTATCTGGAACCCCTGCAGGTTGTGTGTGCACAGAGAGTCATCCTGGCCATGCCGGTCTAC

A   L   N   Q   L   D   W   N   Q   L   R   N   D   R   A   T   Q   A   Y   A   A   V
GCTCT[G]AACCAACT[A]GACTGGAATCAGCTCAGAAATGACCGAGCCACCCAAGCGTACGCTGCCGT[T]
GCTCTCAACCA[GT]TGGA[T]TGGAATCAGCTCAGAAATGACCGAGCCACCCAAGCGTACGCTGCCGTG
GCTCTCAACCAACTGGACTGGAATCAGCTCAGAAATGACCGAGCCACCCAAGCGTACGCTGCCGTG

R   P   I   P   A   S   K   V   F   M  [TS] F   D   Q   P   W   W   L   E   N   E   R
CGCCCGATTCCTGCAAGTAAGGTGTTCATG[T]CCTTTGATCAGCCCTGGTGGTTGGAGAACGAGAGG
CGCCCGATTCCTGCAAGTAAGGTGTTCATGACCTTTGATCAGCCCTGGTGGTTGGAGAACGAGAGG
CGCCCGATTCCTGCAAGTAA[A]GTGTTCATGACCTTTGATCAGCCCTGGTGGTTGGAGAACGAGAGG

K   S   W   V   T   K   S   D   A   L   F   S   Q   M   Y   D   W   Q   K   S   E   A
AAATCCTGGGTCACCAAGTCGGACGCGCTTTTCAGCCAAATGTACGACTGGCAGAAGTCTGAGGCG
AAATCCTGGGTCACCAAGTCGGACGCGCTTTTCAG[T]CAAATGTACGACTGGCAGAAGTCTGAGGCG
AAATCCTGGGTCACCAAGTCGGACGCGCTTTTCAGCCAAATGTACGACTGGCAGAAGTCTGAGGCG

S   G   D   Y   I   L   I   A   S   Y   A   D   G   L   K   A   Q   Y   L   R   E   L
TCCGGAGACTACATCCTGATCGCCAGCTACGCCGACGGCCTCAAAGCCCAGTACCTGCGGGAGCTG
TCCGGAGACTACATCCTGATCGCCAGCTACGCCGACGGCCTCAAAGCCCAGTACCTGCGGGAGCTG
TCCGGAGACTACATCCTGATCGCCAGCTACGCCGACGGCCTCAAAGCCCAGTACCTGCGGGAGCTG

K   N   Q   G   E   D   I   P   G   S   D   P   G   Y   N   Q   V   T   E   P   L   K
AAGAATCAGGGAGAGGACATCCCAGGCTCTGACCCAGGCTACAACCAGGT[T]ACCGAACCCCTCAAG
AAGAATCAGGGAGAGGACATCCCAGGCTCTGACCCAGGCTACAACCAGGTCACCGAACCCCTCAAG
AAGAATCAGGGAGAGGACATCCCAGGCTCTGACCCAGGCTACAACCAGGTCACCGAACCCCTCAAG
```

Figure 11 (continued)

```
        D   T   I   L   D   H   L   T   E   A   Y   G   V   E   R   D   S   I  [PR]  E   P   V
      GACACCATTCTTGACCACCTCACTGAGGCTTATGGCGTGGAGCGAGACTCGATCCCGGAACCCGTG
      GACACCATTCTTGACCACCTCACTGAGGC[C]TATGGCGTGGAGCGAGACTCGATCC[G]GGAACCCGTG
      GACACCATTCTTGACCACCTCACTGAGGCTTATGGCGTGCA[A]CGAGACTCGATCCCGGAACCCGTG

T   A   A   S   Q   F   W   T   D   Y   P   F   G   C   G   W   I   T   W   R   A   G
      ACCGCCGCTTCCCAGTTCTGGACAGACTACCCGTTTGGCTGTGGATGGATCACCTGGAGGGCCGGC
      ACCGCCGCTTCCCAGTTCTGGACAGACTACCCGTTTGGCTGTGGATGGATCACCTGGAGGGCCGGC
      ACCGCCGCTTCCCAGTTCTGGAC[C]GACTACCCGTT[C]GGCTGTGGATGGATCACCTGGAGGGC[A]GGC

F   H   F   D   D   V   I   S   T   M   R   R   P   S   L   K   D   E   V   Y   V   V
      TTCCATTTCGATGACGTCATCAGCACCATGCGTCGCCCGTCACTGAAAGATGAGGT[A]TACGTGGTG
      TTCCATTTCGATGACGTCATCAGCACCATGCGTCGCCCGTCACTGAAAGATGAGGTCTACGTGGTG
      TTCCATTT[T]GATGACGTCATCAGCACCATGCGTCGCCCGTCACTGAAAGATGAGGTCTACGTGGTG

G   A   D   Y   S   W   G   L   I   S   S   W   I   E   G   A   L   E   T   S   E   N
      GGAGCCGA[C]TACTCCTGGGGACTTATCTCCTCCTGGATAGAGGGCGCTCTGGAGACCTCGGAAAAC
      GGAGCCGATTACTCCTGGGGACTTATCTCCTCCTGGATAGAGGGCGCTCTGGAGACCTC[A]GAAAAC
      GGAGCCGATTACTCCTGGGGACTTATCTCCTCCTGGATAGAGGGCGCTCTGGAGACCTCGGAAAAC

V   I   N   D   Y   F   L   -        SEQ ID NO: 2, 4, and 6
      GTCATCAACGACTACTTCCTCTAA    SEQ ID NO: 1
      GTCATCAACGACTACTTCCTCTAA    SEQ ID NO: 3
      GTCATCAACGACTACTTCCTCTAA    SEQ ID NO: 5
```

PEG-MODIFIED ARGININE/LYSINE OXIDOREDUCTASE

CROSS-REFERENCE TO RELATED APPLICATIONS

This application is a continuation of U.S. patent application Ser. No. 12/667,920, filed on Jan. 6, 2010 and titled PEG-MODIFIED ARGININE/LYSINE OXIDOREDUCTASE, which is the U.S. national stage of International Patent Application No. PCT/EP2007/004587, filed on May 23, 2007 and titled PEG-MODIFIED ARGININE/LYSINE OXIDOREDUCTASE, which claims the benefit of priority from European Patent Application No. 06010824.8, filed on May 26, 2006 and titled PEG-MODIFIED ARGININE/LYSINE OXIDOREDUCTASE. The disclosures of the foregoing applications are incorporated herein by reference in their entirety.

SEQUENCE LISTING

The entire content of a Sequence Listing titled "Sequence_Listing.txt," created on Sep. 6, 2013 and having a size of 48 kilobytes, which has been submitted in electronic form in connection with the present application, is hereby incorporated by reference herein in its entirety.

FIELD OF THE INVENTION

The present invention is directed to an arginine/lysine oxidoreductase modified with polyethylene glycol.

BACKGROUND OF THE INVENTION

Since decades, tremendous efforts are made to collect pharmacologically active substances from natural organisms and to test their effects in various disease areas.

The sea hare *Aplysia punctata* produces a purple ink to protect itself from predation. This ink was shown to contain an anti-tumor activity (Butzke et al., 2004). Subsequently, studies were conducted to isolate the factor from crude ink, resulting in the discovery of APIT, the *Aplysia Punctata* Ink Toxin. Recently, the factor was cloned and characterized to be a weakly glycosylated FAD-binding L-amino acid oxidase that catalyzes the oxidative deamination of L-lysine and L-arginine and thereby produces hydrogen peroxide ($H_2O_2$), ammonium ($NH_4^+$) and the corresponding alpha-keto acids (Butzke et al., 2005).

L-amino acid oxidases (LAAOs, EC 1.4.3.2), can be found in secretions and venoms. Members of this family of flavoenzymes catalyze the stereospecific oxidative deamination of L-amino acids and thereby produce $H_2O_2$, ammonium and the corresponding alpha-keto acids (Du et al., 2002). The 3D individual LAAOs differ in their substrate specificity: Snake venom L-amino acid oxidases (sv-LAAOs) which constitute up to 30% (by weight) of the crude venom (Ponnudurai et al., 1994), possess a clear preference for hydrophobic amino acids. A fish capsule LAAO termed AIP (Apoptosis-Inducing Protein) which is induced by larval nematode infection of *Scomber japonicus* is highly specific for L-lysine (Jung et al., 2000). Achacin, a mucus LAAO from the African snail *Achatina fulica*, metabolizes a very broad range of substrates, including hydrophobic amino acids along with L-lysine, L-arginine, L-cysteine, L-asparagine and L-tyrosine (Ehara et al., 2002).

L-amino acid oxidases have not been investigated for their half-life after administration to mammalians at any routes. With respect to drug development, this is however an important issue and a prerequisite to efficiently exert a therapeutic effect. Data in this respect are only available for a D-amino acid oxidase employing D-proline as substrate (Fang et al., 2002). After intravenous injection, native D-amino acid oxidase was, however, rapidly cleared from the circulation. A pegylated derivative did not exhibit a significantly increased circulation half-life time which was well below 1 h. A product with such a short circulation half life time cannot be expected to have a substantial therapeutic benefit for therapy, e.g. for cancer therapy. Thus, according to the teaching of the prior art it would have been expected that pegylated amino acid oxidases would lack therapeutically efficacy.

An object of the present invention was to increase the therapeutic efficacy of L-amino acid oxidoreductases in order to provide a therapeutic product with improved characteristics.

SUMMARY OF THE INVENTION

The present invention addresses for the first time an arginine/lysine oxidoreductase modified with at least one polyethylene glycol moiety and pharmaceutical compositions comprising said modified arginine/lysine oxidoreductase, a production method thereof and methods to treating diseases responsive to modulation of plasma amino acid levels or/and responsive to reactive oxygen species or/and ammonium, for example proliferative diseases, viral infections or/and microbial infections.

In a preferred embodiment, an arginine/lysine oxidoreductase termed *Aplysia punctata* ink toxin (APIT) is modified with at least one polyethylene glycol moiety having a weight average molecular weight of from about 1,000 to about 10,000.

An additional embodiment of the invention describes methods of production of a pegylated arginine/lysine oxidoreductase.

A further embodiment describes a method of enhancing the enzymatic activity and circulation time of an arginine/lysine oxidoreductase comprising pegylation of an arginine/lysine oxidoreductase.

An additional embodiment refers to a method of protecting an arginine/lysine oxidoreductase against inactivation by body fluids comprising pegylation of an arginine/lysine oxidoreductase.

In a further aspect, the present invention refers to a method for depleting the amino acids lysine or/and arginine in a liquid, comprising adding an arginine/lysine oxidoreductase to the liquid.

Yet another embodiment refers to a kit comprising an arginine/lysine oxidoreductase of the present invention.

DETAILED DESCRIPTION OF THE INVENTION

The object of the present invention is achieved by covalently modifying arginine/lysine oxidoreductases, particularly L-arginine/lysine oxidases, with polyethylene glycol (PEG). The present invention is based on the surprising discovery that arginine/lysine oxidoreductases modified with polyethylene glycol are circulating in the plasma of mice for more than 48 h and retain their enzymatic activity. In contrast, unmodified arginine/lysine oxidoreductases are active in circulation for only about 3 h at equivalent activity-based dose.

Furthermore, it was surprisingly found that dosing of a PEG modified arginine/lysine oxidoreductase can be significantly reduced compared with the unmodified arginine/lysine oxidoreductase.

Moreover, it was surprisingly found that PEG modified arginine/lysine oxidoreductase has a smaller IC50 value for inhibition of lung cancer cells than unmodified arginine/lysine oxidoreductase.

Furthermore, arginine/lysine oxidoreductases modified with polyethylene glycol provide a unique means in lowering amino acid levels lysine and arginine thereby producing reactive oxygen species and ammonium. All these effects or parts thereof are sufficient to treat certain types of disorders. When compared to a native arginine/lysine oxidoreductase, a pegylated arginine/lysine oxidoreductase retains most of its enzymatic activity, is able to deplete lysine and arginine in mammalians for 48 h and more, and is much more efficacious in the treatment of diseases responsive to a modification of amino acid levels and/or reactive oxygen species or ammonium. Moreover, the pegylated arginine/lysine oxidoreductase is active even in the presence of specific antibodies directed to the unmodified arginine/lysine oxidoreductase.

In a first aspect, the present invention provides a conjugate comprising an arginine/lysine oxidoreductase and at least one polyethylene glycol moiety.

"Conjugate" as used herein refers to a compound which comprises a polypeptide portion preferably including a coenzyme such as FAD to which at least one polyethylene glycol moiety has been coupled by a covalent linkage.

The conjugate of the present invention may comprise any known arginine/lysine oxidoreductase, particularly L-arginine/lysine oxidoreductase, which catalyzes the conversion of L-arginine or/and L-lysine into the respective alpha imino acid. In this step, the enzyme produces $H_2O_2$ in stoichiometric amounts. In a second step, the alpha imino acid is converted into an alpha keto acid under release of ammonium. The second step is not dependent upon the arginine/lysine oxidoreductase activity. Details of the reaction catalyzed by arginine/lysine oxidoreductase are described in WO 2004/065415 which is included herein by reference.

In another preferred embodiment of the present invention, the conjugate comprises an arginine/lysine oxidoreductase which is an L-arginine/L-lysine oxidoreductase.

In a further preferred embodiment, the conjugate comprises an arginine/lysine oxidoreductase which is specific for arginine or/and lysine. In particular, the enzymatic activity for the processing of lysine or/and arginine, in particular L-lysine or/and L-arginine, is at least a factor of about 3 or about 4 larger than the enzymatic activity for the processing of other amino acids, in particular of alpha-L-amino acids naturally present in organisms.

A preferred arginine/lysine oxidoreductase may be obtained from an *Aplysia* species, in particular from *Aplysia punctata*. For example, the *Aplysia Punctata* Ink Toxin (APIT), which is an arginine/lysine oxidoreductase of the present invention, can be found in the ink of the sea hare *Aplysia punctata*. This enzyme and its manufacture is described in WO 2004/065415 which is included herein by reference.

Further, a suitable L-lysine α-oxidase is described in Lukasheva E V, Berezov T T. L-Lysine alpha-oxidase: physiochemical and biological properties. Biochemistry (Mosc.) 2002 October; 67(10):1152-8.

The arginine/lysine oxidase may be a native molecule isolated from a natural source or a recombinant molecule obtained from a recombinant, e.g. non-naturally occurring source. In a preferred embodiment, the conjugate may also comprise a recombinant arginine/lysine oxidoreductase.

In an especially preferred embodiment, the conjugate of the present invention comprises an arginine/lysine oxidoreductase comprising (a) the sequence SEQ ID NO: 2, 4, 6, or/and 8,
(b) a sequence with at least which is at least 70% identical to the sequence of (a), or/and
(c) a fragment of (a) or/and (b).

SEQ ID NO: 2, 4, 6, and 8 differ in several amino acid positions. SEQ ID NO: 8 describes a preferred arginine/lysine oxidoreductase isolated from *Aplysia punctata* (see examples of the present invention). SEQ ID NO: 2, 4, and 6 describe further arginine/lysine oxidoreductases isolated from *Aplysia punctata*. SEQ ID NO: 2, 4, and 6 are described in WO 2004/065415 which is included herein by reference.

The preferred sequence of (a) is SEQ ID NO: 8.

The sequence of (b) is a sequence which is at least 70%, preferably at least 80%, more preferably at least 90%, even more preferably at least 95%, most preferably at least 99% identical to the sequence of (a). The identity is determined in the region of maximal overlap. The person skilled in the art can determine the region of maximal overlap by commonly known algorithms such as FASTA, BLAST or/and derivatives thereof relating to amino acid sequences.

The fragment of (c) is any enzymatically active fragment of an arginine/lysine oxidoreductase of (a) or (b) and may have a length of a least about 30 amino acid residues, preferably at least about 50 amino acid residues, more preferably at least about 100 amino acid residues, most preferably at least about 200 amino acid residues.

The fragment of (c) may have a length of smaller than the full length of SEQ ID NO: 2, 4, 6, or/and 8, preferably at the maximum about 500 amino acid residues, more preferably at the maximum about 400 amino acid residues, most preferably at the maximum about 300 amino acid residues.

The fragment of (c) may be selected from sequences derived from SEQ ID NO: 2, 4, 6 or/and 8 by removing N-terminal amino acids. The N-terminus may represent signal sequences which are not required for the oxidoreductase function. Preferably, up to about 5, up to about 10, up to about 20, or up to about 50 N-terminal amino acids are removed. More preferably, in SEQ ID NO: 2, 18 N-terminal amino acids are removed, or/and in SEQ ID NO:4, 17 N-terminal amino acids are removed.

The conjugate of the present invention is preferably active in the circulation for at least 6 h, i.e. the conjugate has preferably a circulation time of at least 6 h. In the context of the present invention, "circulation time" refers to the time the conjugate of the present invention retains its activity, in particular its enzymatic activity, during circulation in a subject. In the present invention, the term "circulation time" is also applied to other compounds for comparative purposes. For instance, "circulation time" is applied to unmodified APIT. The circulation time may also be expressed by the circulation half life time.

The conjugate of the present invention is more preferably active in the circulation for at least 12 h, even more preferably at least 24 h, most preferably at least 48 h.

It was surprisingly found that the dose of the conjugate of the present invention can significantly be reduced compared with the corresponding unmodified arginine/lysine oxidoreductase. For instance, an amount of 0.6 Units/kg PEG-5000-APIT is capable of depleting lysine and arginine levels in blood plasma in mice for 6 h. Unmodified APIT requires 1000 Units/kg to achieve the same effect. Thus the dose of PEG-5000-APIT can be reduced by a factor of about 1667 compared with unpegylated APIT. In other words, the activity of PEG-5000-APIT is a factor of about 1667 larger than the activity of unmodified APIT.

Therefore, in a preferred embodiment, the activity of the conjugate of the present invention is a factor of at least 30, preferably at least 100, more preferably at least 300, even more preferably at least 1000, most preferably at least 1500 larger than the activity of the arginine/lysine oxidoreductase not carrying a polyethylene glycol moiety. The activity is in particular the enzymatic activity. More particularly the activity is the enzymatic activity in the blood plasma after administration to a subject, for instance a mammal such as a rodent or a human. The enzymatic activity may be determined by determination of the dose required to deplete arginine or/and lysine in a liquid, for instance a body fluid such as blood plasma, for a predetermined length of time The length of time may be selected from ranges of about 3 to about 48 h, about 6 to about 24 h, or about 12 to about 18 h, or may preferably be about 3 h, about 6 h, about 12 h, about 24 h, or about 48 h. Arginine or/and lysine may be depleted to a predetermined level, for instance 0 μM. The predetermined level may be selected from a range of 0 μM to about 10 μM, 0 μM to 20 μM, or 0 μM to about 100 μM.

The factor of activity improvement can for instance be calculated by dividing the dose of the unpegylated arginine/lysine oxidoreductase by the dose of the conjugate of the present invention, which doses are required for depletion of arginine or/and lysine for a predetermined length of time.

In a further preferred embodiment, the conjugate of the present invention comprises at least one polyethylene glycol moiety having a weight average molecular weight of about 1,000 Dalton to about 10,000 Dalton, preferably of about 3,000 Dalton to about 8,000 Dalton, more preferably of about 4,000 Dalton to about 6,000 Dalton, even more preferably about 4,500 Dalton to about 5,500 Dalton, most preferably about 5,000 Dalton.

The polyethylene glycol moiety as employed herein includes unmodified and modified polyethylene glycol moieties suitable for coupling to polypeptides. The modified polyethylene glycol moieties preferably include terminally modified polyethylene glycol moieties, wherein the terminal OH group has been modified, e.g. by alkylation, acylation and/or oxidation. More preferably, the polyethylene glycol moieties have terminal OH groups or modified terminal groups selected from O—$C_{1-3}$ alkyl groups and acyl groups or combinations thereof.

In yet another preferred embodiment, the conjugate comprises at least one polyethylene glycol moiety which is covalently coupled to the arginine/lysine oxidoreductase via a linking group. The linking group may be a succinimide group, preferably a succinimidyl succinate group.

In yet another preferred embodiment, the conjugate of the present invention comprises from 1 to about 30 polyethylene glycol moieties, preferably from 1 to about 20 polyethylene glycol moieties, more preferably from 1 to about 10 polyethylene glycol moieties.

In the conjugate of the present invention, the at least one polyethylene glycol group may be coupled to any amino acid with a side chain carrying a reactive functional group, such as a carboxylate group, amino group, thiol group and/or hydroxy group, for example an amino acid selected from aspartate, glutamate or/and lysine. A preferred embodiment refers to a conjugate wherein the at least one polyethylene glycol moiety is coupled via a lysine residue to the arginine/lysine oxidoreductase. Since SEQ ID NO: 8 comprises 23 lysine residues, a conjugate of the present invention comprising a polypeptide of SEQ ID NO: 8 may comprise up to 23 polyethylene glycol moieties, preferably up to about 10 polyethylene glycol moieties coupled via a lysine residue.

It is more preferred that in the conjugate of the present invention, the at least one polyethylene group is coupled to lysine via a linker group, e.g. a succinimide linker group or any other suitable linker group for coupling to amino groups. It is even more preferred that in the conjugate of the present invention, the at least one polyethylene group has a weight average molecular weight of about 4,500 to about 5,500 Dalton and is coupled to lysine by via a linker group, e.g. a succinimide linker group.

Most preferred is a conjugate comprising an L-arginine/L-lysine oxireductase comprising SEQ ID NO: 8 and at least one polyethylene glycol group having a weight average molecular weight of about 4,500 to 5,500 Dalton.

Yet another aspect is a method of producing the conjugate of the present invention, comprising the steps
(a) recombinantly expressing an arginine/lysine oxidoreductase or/and isolating an arginine/lysine oxidoreductase from a natural source,
(b) coupling at least one polyethylene glycol moiety to the arginine/lysine oxidoreductase of (a).

Preferred natural sources of an arginine/lysine oxidoreductase which may be employed in step (a) are as described above.

Step (a) preferably comprises a recombinant expression of a nucleic acid comprising
(i) the sequence SEQ ID NO: 1, 3, 5, or/and 7,
(ii) a sequence complementary to the sequence of (i),
(iii) a sequence within the scope of the degeneracy of the genetic code of the sequence of (i) or (ii),
(iv) a sequence which is at least 70% identical to the sequence of (i), (ii) or/and (iii),
(v) a sequence which hybridizes with any of the sequences (i), (ii), (iii) or/and (iv) under stringent conditions, or/and
(vi) a fragment of any of the sequences (i), (ii), (iii), (iv), or/and (v).

SEQ ID NO: 1, 3, 5, and 7 are nucleic acid sequences encoding polypeptides comprising the amino acid sequences SEQ ID NO: 2, 4, 6, and 8, respectively. SEQ ID NO: 1, 3, 5, and 7 differ in several nucleotide positions. SEQ ID NO: 7 describes the nucleotide sequence encoding an arginine/lysine oxidoreductase isolated from *Aplysia punctata* (see examples of the present invention). SEQ ID NO:1, 3, and 5 describe further nucleotide sequences encoding arginine/lysine oxidoreductases isolated from *Aplysia punctata*. SEQ ID NO:1, 3, and 5 are described in WO 2004/065415 which is included herein by reference.

A preferred sequence of (i) is SEQ ID NO: 7.

The nucleotide sequence of (iv) is a sequence which is at least 70%, preferably at least 80%, more preferably at least 90%, even more preferably at least 95%, most preferably at least 99% identical to the sequence of (i), (ii) or/and (iii). The identity of the nucleotide sequences is determined within the region of maximal overlap. A person skilled in the art can easily determine the region of maximal overlap by commonly known algorithms such as FASTA or BLAST.

The person skilled in the art knows stringent hybridization conditions (see e.g. Sambrook J. et al., 1989, Molecular Cloning, A Laboratory Manual, Cold Spring Harbor Press, Plainview, N.Y). Hybridization under stringent conditions in step (v) preferably means that after washing for 1 h with 1×SSC and 0.1% SDS at 55° C., preferably at 62° C. and more preferably at 68° C., particularly after washing for 1 h with 0.2×SSC and 0.1% SDS at 55° C., preferably at 62° C. and more preferably at 68° C., a hybridization signal is detected.

The fragment of (vi) may have a length of a least about 90 nucleotide residues, preferably at least about 150 nucleotide residues, more preferably at least about 300 nucleotide residues, most preferably at least about 600 nucleotide residues.

The fragment of (vi) may have a length of smaller than the full length of SEQ ID NO: 1, 3, 5, or/and 7, preferably at the maximum about 1500 nucleotide residues, more preferably at the maximum about 1200 nucleotide residues, most preferably at the maximum about 900 nucleotide residues.

The fragment of (vi) may be selected from sequences derived from SEQ ID NO: 1, 3, 5 and 7 by removing 5' nucleotides encoding the N-terminal amino acids which may represent signal sequences which are not required for the oxidoreductase function. Preferably, up to about 15, up to about 30, up to about 60, or up to about 150 5' nucleotides are removed. More preferably, in SEQ ID NO: 1, 54 5' nucleotides are removed, or/and in SEQ ID NO:3, 51 5' nucleotides are removed.

The person skilled in the art knows methods for recombinant expression of a protein, isolation, refolding and introduction of prosthetic groups such as FAD. In the examples of the present invention the recombinant expressing of SEQ ID NO: 7 is described in order to obtain a polypeptide comprising SEQ ID NO: 8. Preferred host cells for recombinant expression are prokaryotic or eukaryotic host cells, e.g. yeast cells or bacterial cells, particularly Gram-negative bacterial cells, such as *E. coli*.

The method for the preparation of the conjugate of the present invention may further comprise the introduction of a coenzyme such as FAD into the arginine/lysine oxidoreductase.

Step (b) of the method for the preparation of the conjugate of the present invention refers to coupling of at least one polyethylene glycol moiety to the arginine/lysine oxidoreductase obtained in step (a). Pegylation in step (b) may be performed by standard procedures known by a person skilled in the art.

In step (b), a polyethylene glycol may be employed having a weight average molecular weight of about 1,000 Dalton to about 10,000 Dalton, preferably of about 3,000 Dalton to about 8,000 Dalton, more preferably of about 4,000 Dalton to about 6,000 Dalton, even more preferably about 4,500 Dalton to about 5,500 Dalton, most preferably about 5,000 Dalton.

The polyethylene glycol moiety may be covalently bound via a linking group, which may be a succinimide group, preferably a succinimidyl succinate. Other linking groups may also be employed. The person skilled in the art knows suitable linking groups.

It is preferred that the at least one polyethylene glycol moiety is coupled via a lysine residue to the arginine/lysine oxidoreductase. Coupling to lysine can be performed by applying a succinimide linker group. Coupling may also performed to other amino acid side chains carrying a functional group such as a carboxylase group, amino group, thiol group or/and hydroxy group, such as aspartate or glutamate.

In order to provide a conjugate of the present invention comprising from 1 to about 30 polyethylene glycol moieties, preferably from 1 to about 20 polyethylene glycol moieties, more preferably from 1 to about 10 polyethylene glycol moieties, an excess of polyethylene glycol may be employed in step (b). The polyethylene glycol may be provided in an amount of from about 10 to about 500 equivalents, preferably from about 10 to about 50 equivalents with respect to the number of free residues available for coupling, for instance the number of free lysine residues. In particular, about 10, about 20, about 30, about 40, about 50, about 200, or about 500 equivalents polyethylene glycol may be employed. An excess of 50 equivalents may result in coupling of about 10 PEG molecules per molecule arginine/lysine oxidoreductase.

Yet another aspect of the present invention is a pharmaceutical composition comprising a conjugate of the present invention optionally together with pharmaceutically acceptable carriers, adjuvants, diluents or/and additives.

The pharmaceutical composition of the present invention may be suitable for the prevention, alleviation or/and treatment of a disease responsive to reactive oxygen species or/and ammonium, or/and responsive to modulation of plasma amino acid levels, in particular of plasma lysine or/and arginine levels. The pharmaceutical composition of the present invention may also be suitable for the prevention, alleviation or/and treatment of a disease selected from microbial infections, viral infections such as HIV, hepatitis B or/and C virus infections, and proliferative diseases such as cancer.

The pharmaceutical composition of the present invention is suitable for the treatment of solid tumors and leukemias in general including apoptosis resistant and multi drug resistant cancer forms.

The proliferative disease to be treated with the pharmaceutical composition of the present invention may be lung cancer, MDR lung cancer, head and neck cancer, breast cancer, prostate cancer, colon cancer, cervix cancer, uterus cancer, larynx cancer, gastric cancer, liver cancer, Ewings sarcoma, acute lymphoid leukemia, acute and chronic myeloid leukemia, apoptosis resistant leukemia, pancreas cancer, kidney cancer, gliomas, melanomas, chronic lymphoid leukemia, or/and lymphoma.

Yet another aspect of the present invention is a method for the prevention, alleviation or/and treatment of a disease responsive to reactive oxygen species, ammonium or/and responsive to modulation of amino acid levels in body fluids, in particular of plasma lysine or/and arginine levels, which method comprises administering an effective amount of the conjugate of the of the present invention or/and a pharmaceutical composition of the present invention to a subject in need thereof. The disease to be treated by the method is in particular a microbial infection, a viral infection or/and a proliferative disease as defined above.

Yet another aspect of the present invention is a kit comprising the conjugate of the present invention or/and the pharmaceutical composition of the present invention.

A further aspect of the present invention refers to a method for enhancing the enzymatic activity or/and circulation time of an arginine/lysine oxidoreductase, which method comprises coupling at least one polyethylene glycol moiety to the arginine/lysine oxidoreductase. In this method, the arginine/lysine oxidoreductase may in particular be the arginine/lysine oxidoreductase as defined herein. The polyethylene glycol moiety may be as defined herein.

Yet a further aspect of the present invention is a method for protecting an arginine/lysine oxidoreductase against inactivation in body fluids such as blood plasma comprising coupling at least one polyethylene glycol moiety to the arginine/lysine oxidoreductase. In this method, the arginine/lysine oxidoreductase may in particular be the arginine/lysine oxidoreductase as defined herein. The polyethylene glycol moiety may be as defined herein. In particular, inactivation in body fluids may be inactivation by antibodies.

A PEG group, in particular a PEG group as described herein, may be used for enhancing the enzymatic activity or/and circulation time of an arginine/lysine oxidoreductase, in particular of an arginine/lysine oxidoreductase as defined herein.

A PEG group, in particular a PEG group as described herein, may be used for protecting an arginine/lysine oxidoreductase, in particular an arginine/lysine oxidoreductase as defined herein against inactivation in body fluids such as blood plasma, in particular by antibodies.

The conjugate of the present invention as defined herein or/and the pharmaceutical composition of the present invention as defined herein may be used for the depletion of lysine or/and arginine in a liquid or/and for the production of hydrogen peroxide, ammonium or/and metabolites of lysine or/and arginine in a liquid. The liquid may in particular be a body fluid of a mammal.

The invention is further demonstrated in the following examples and figures, which are for purposes of illustration, and are not intended to limit the scope of the present invention.

FIGURE LEGENDS

FIG. 1: Primary amino acid sequence of arginine/lysine oxidoreductase, APIT (SEQ ID NO: 8) and a nucleotide sequence coding therefor (SEQ ID NO:7).

FIG. 2: Pegylation of arginine/lysine oxidoreductase, APIT with PEG-5000.

Figure 3:
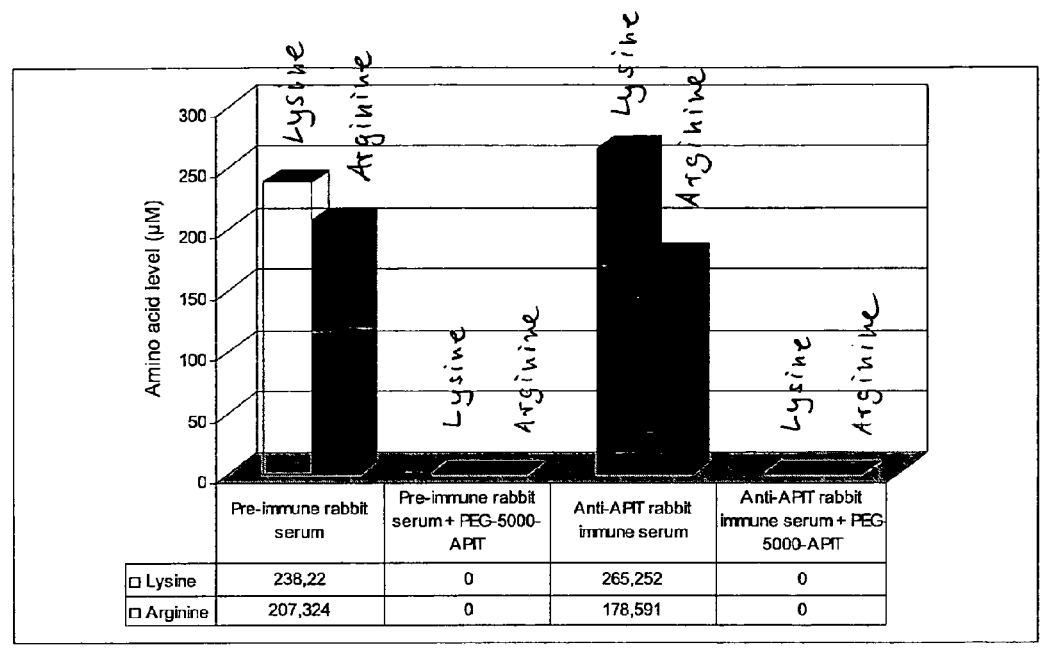

FIG. 3: Activity of PEG-5000-APIT in the presence of anit-APIT polyclonal antibodies.

Figure 4:
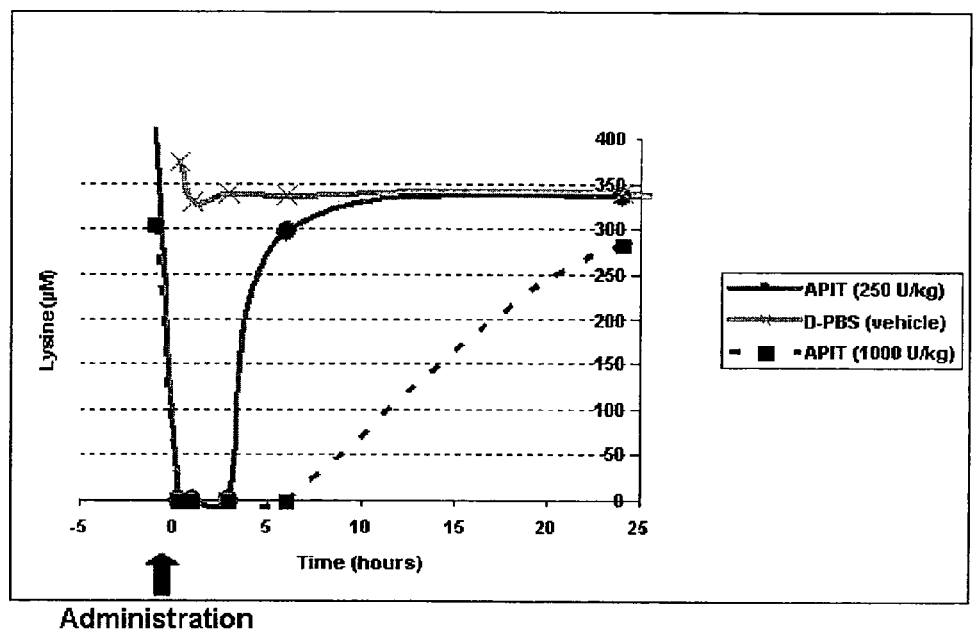

FIG. 4: Effect of single intravenous dose of APIT (250 U/kg) and APIT (1000 U/kg) on plasma lysine levels in mice.

Figure 5:
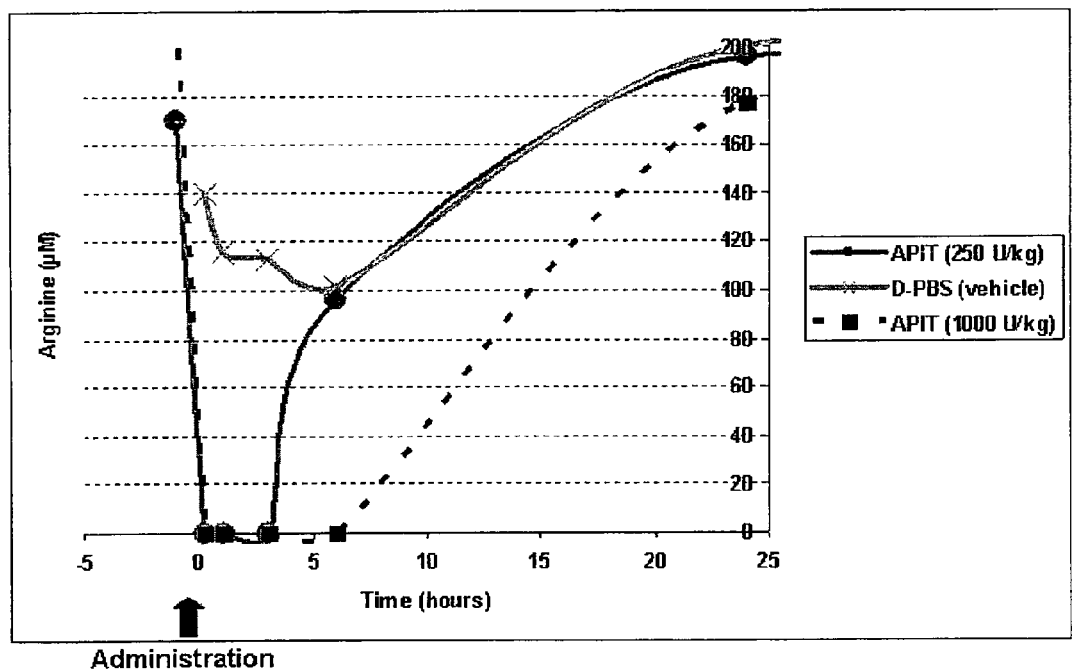

FIG. 5: Effect of single intravenous dose of APIT (250 U/kg) and APIT (1000 U/kg) on plasma arginine levels in mice.

Figure 6:
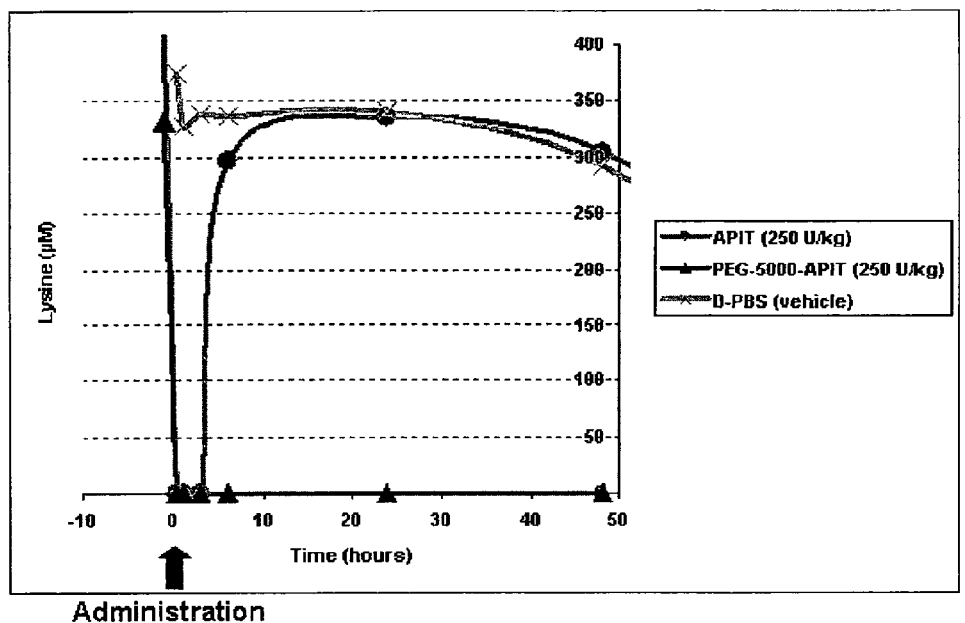

FIG. 6: Comparison of single intravenous dose of APIT (250 U/kg) and PEG-5000-APIT at an equivalent dose of 250 U/kg on plasma lysine levels in mice.

Figure 7:
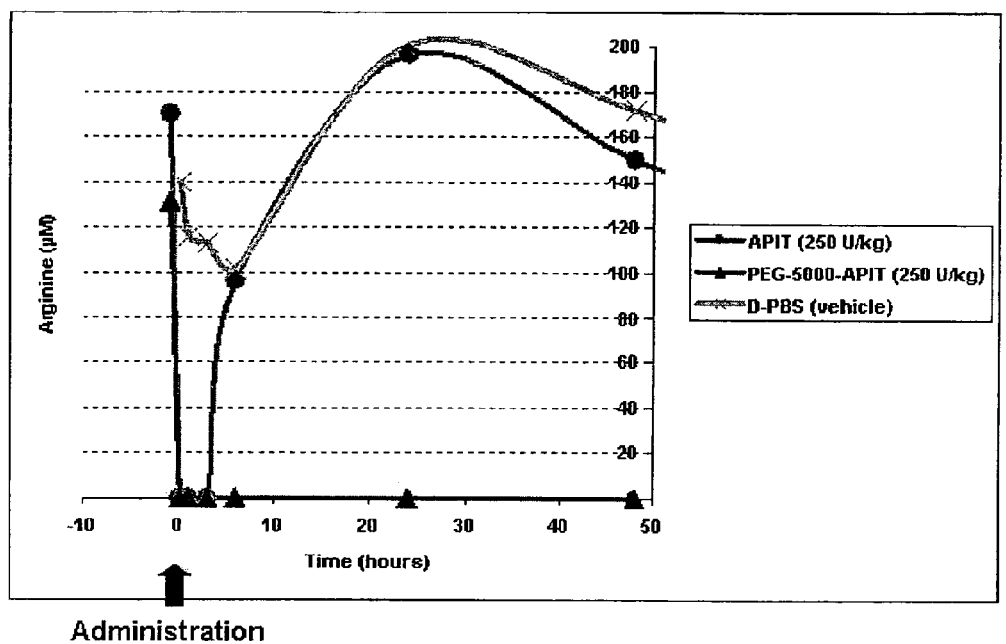

FIG. 7: Comparison of single intravenous dose of APIT (250 U/kg) and PEG-5000-APIT at an equivalent dose of 250 U/kg on plasma arginine levels in mice.

Figure 8:
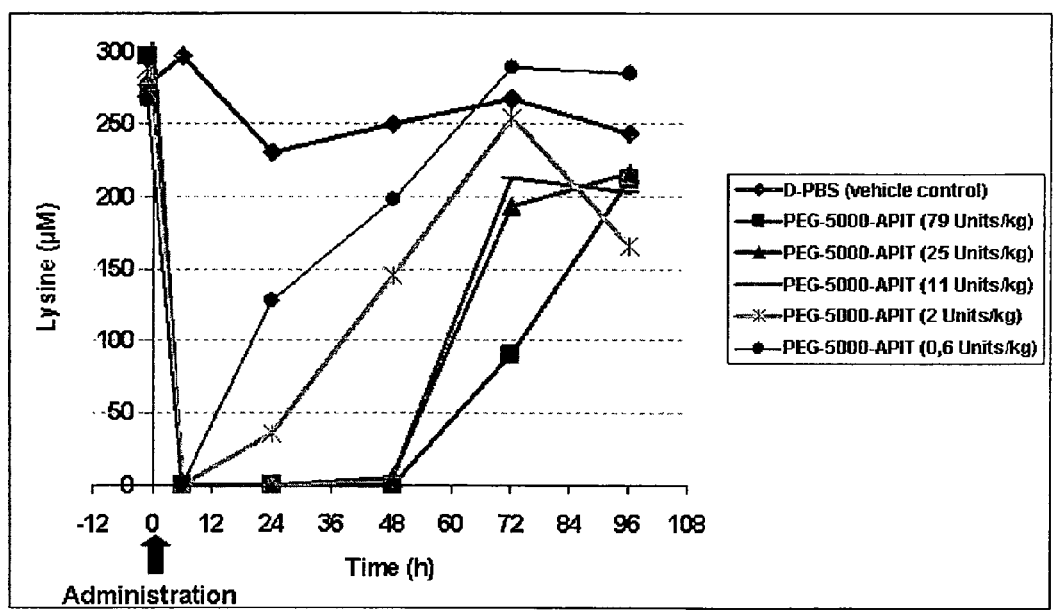

FIG. 8: Dose-dependent depletion of plasma lysine levels after single intravenous administration of PEG-5000-APIT to mice.

Figure 9:
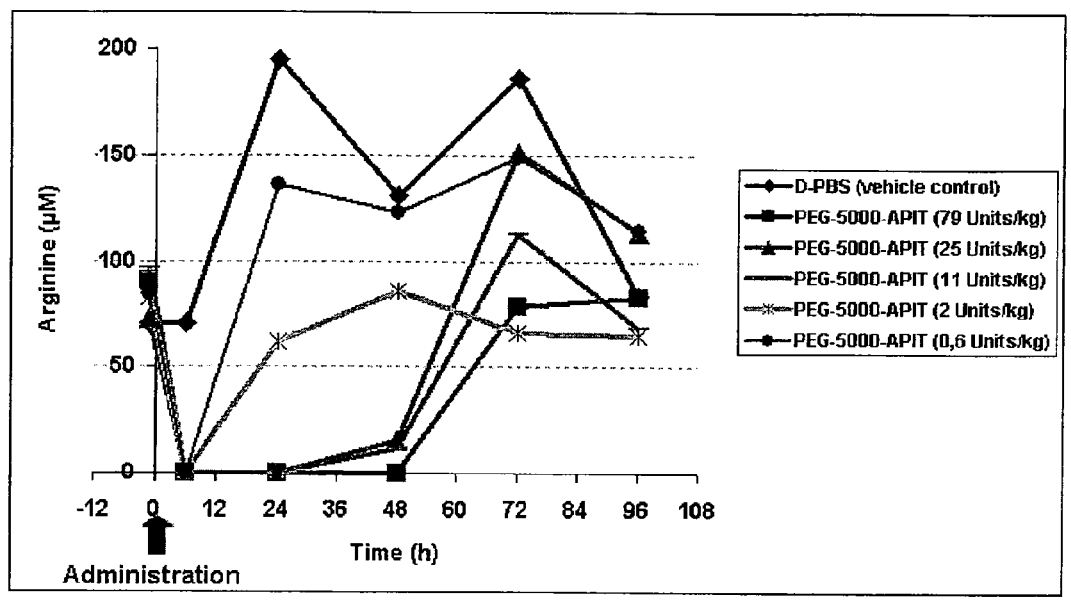

FIG. 9: Dose-dependent depletion of plasma arginine levels after single intravenous administration of PEG-5000-APIT to mice.

Figure 10:
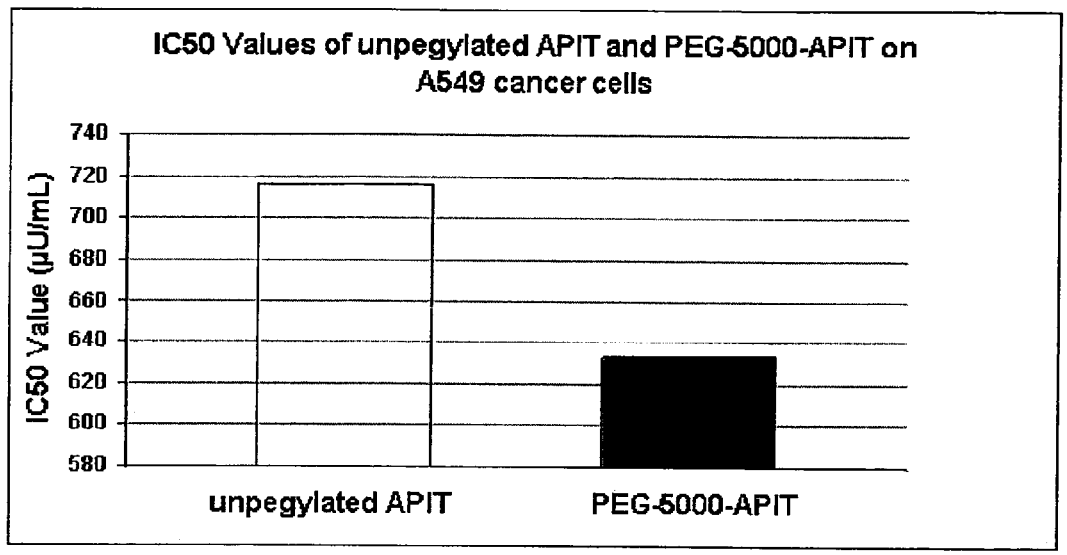

FIG. 10: Antitumor efficacy of PEG-5000-APIT.

FIG. 11: Nucleotide sequences of cDNA encoding arginine/lysine oxidoreductases isolated from ink of *Aplysia punctata* (SEQ ID NO: 1, 3 and 5) and the derived amino acid sequences (SEQ ID NO: 2, 4, and 6). The dinucleotide binding fold (28 amino acid residues) and the GG motif (8 amino acid residues) are indicated by boxes.

EXAMPLES

Example 1

Method of Bulk Production of Recombinant Arginine/Lysine Oxidoreductase, APIT in *E. coli*

A B-Braun Biostat B10 Fermenter with 5000 ml medium is inoculated with a working cell starter culture containing the APIT-cDNA comprising SEQ ID NO: 7 under control of a suitable promoter (e.g. T7). Cells are grown up to an optical density of 6-8 (at 600 nm) at 37±0.5° C. Subsequently the cells are induced through the addition of IPTG and further fermented for additional 3 h at 37±0.5° C. Thereafter, cells are harvested through centrifugation and stored at ≤−60° C. The resuspended cells are disrupted using a French press and the inclusion bodies are separated from the supernatant by centrifugation. The inclusion bodies are stored up to further processing at ≤−60° C. APIT is isolated with urea from the inclusion bodies of the *E. coli* biomass. The solubilized protein is then refolded, concentrated and desalted by TFF (Tangential Crossflow Filtration). Subsequently, APIT is purified by anion exchange chromatography and size exclusion chromatography (SEC).

Isolation of APIT from Inclusion Bodies:

The pellet is resuspended two times in succession in washing-buffer, then NaCl-Washing-buffer and Urea-washing-buffer. The suspension is centrifuged following each resuspension-step, while the remaining supernatant is discarded. Thereafter, the pellet is resuspended in Resuspensions-Buffer following a final centrifugation step. The supernatant is filtrated through 0.2 µm and the (APIT-containing) solution is stored frozen at <−15° C.

Refolding:

This process step is carried out at room temperature (22-25° C.). 200 mL of the isolated APIT from *E. coli* (in Resuspension-Buffer) are mixed with 200 mL Guanidine-HCl. This mixture is then injected into 20 L refolding buffer containing L-arginine and FAD, using a pump. The mixing/dilution step is supported by a (maximal active) magnet stirrer. Die dilution is realized via 4 Injection sites.

Purification by TFF:

The RF-mixture is filtered using a TFF (0.2 µm) to separate unfolded protein. Thereafter, the system is rinsed with 1.6 L Tris-Buffer. APIT is concentrated using a 10 kDa-Membrane. Thereafter, the RF-Buffer is dialyzed against the Tris-Buffer. During this step, the conductivity of the RF-mixture and Tris-buffered mixture is measured. The 10 kDa-Membrane is maintained to change the buffer and to continue the concentration step. The level of conductivity decrease in the concentrated APIT solution indicates the duration of the procedure.

Anion-Exchange Chromatography:

The APIT containing sample is further purified by anion-exchange chromatography (SOURCE 30Q-column). The elution of the product from the column is done using a salt-gradient (0-500 mM NaCl) at pH 8.0. The elute is collected in fractions.

Size Exclusion Chromatography:

The APIT-containing sample is desalted using a size exclusion chromatography (Sephadex G25). The purification occurs with D-PBS. The eluted product is collected in fractions.

Filling and Storage:

The filling of the bulk product is in sterile PE-containers at a volume of 1.000 µl and stored at 2-8° C. The primary amino acid sequence of recombinant APIT is shown in FIG. 1.

Example 2

Pegylation of Arginine/Lysine Oxidoreductase, APIT with PEG-5,000

Purified arginine/lysine oxidoreductase, APIT from Example 1 was desalted with HiPrep Desalting 26/10 column and brought into a pegylation reaction buffer containing 50 mM sodiumbicarbonat, pH 9.5. The pegylation reactions were carried by adding a linear polydisperse polyethyleneglycol succinimidylester, MW 5000 Da (PEG-5000-SS) at varying ratios of PEG-5000-SS to arginine/lysine oxidoreductase (based on free lysine residues in APIT) from 10 to 50 equivalents (eq) and stirring for 1 hour at 800 rpm and 25° C. The PEG-conjugated arginine/lysine oxidoreductase variants, PEG-5000-APIT (10 eq), PEG-5000-APIT (20 eq), PEG-5000-APIT (40 eq), PEG-5000-APIT (50 eq) were individually purified by gelfiltration from reaction-products and unconjugated PEG-reagent and the buffer was exchanged to sodium phosphate buffered saline PH 7). The final products were analyzed on SDS-page and for enzymatic activity (FIG. 2). An excess of 50 eq PEG resulted in coupling of about 10 molecules PEG to one molecule APIT.

FIG. 2 shows that the PEG-5000-APIT had an apparent molecular weight ranging from 60 kda to >212 kDa. All PEG-5000-APIT variants were enzymatically active in comparison to unconjugated APIT. The relative enzymatic activities of PEG-5000-APIT (10 eq), PEG-5000-APIT (20 eq), PEG-5000-APIT (40 eq), PEG-5000-APIT (50 eq) ranged from 58% to 72%.

Example 3

Activity in the Presence of Anti-APIT Polyclonal Antibodies

A high titer (>1:200,000) polyclonal antibody serum against APIT was raised in rabbits. In order to investigate if PEG-5000-APIT is inactivated by antibodies against APIT, pre-immune rabbit serum and anti-APIT rabbit immune serum was incubated with PEG-5000-APIT for 1 h at 37° C. following analysis of amino acid levels for lysine and arginine. FIG. 3 shows that lysine and arginine levels in rabbit pre-immune rabbit serum and anti-APIT rabbit immune serum were normal (lysine: 238 µM and 265 µM respectively; arginine 207 µM and 179 µM respectively). Incubation with PEG-5000-APIT resulted in levels of lysine and arginine of 0 µM in both, pre-immune rabbit serum and anti-APIT rabbit immune serum demonstrating that PEG-5000-APIT is enzymatically active in the presence of anti-APIT polyclonal antibodies and allows for complete depletion of lysine and arginine in liquids.

Example 4

Application to Mice

Mice received a single intravenous administration (tail vein) of unconjugated APIT (250 U/kg or 1000 U/kg) or PEG-5000-APIT (250 U/kg, 79 U/kg, 11 U/kg, 2 U/kg, 0.6 U/kg) or D-PBS (vehicle control) respectively. Serial blood samples were collected from each animal via orbital sinus under etherization at −1 h pre-dose and at the indicated timepoints post-dose and transferred into tubes containing anticoagulant (heparin). Each blood sample was centrifuged at 4° C. to prepare plasma for analysis of plasma amino acid levels.

For the amino acid analysis, 25 µL heparin plasma samples were mixed with 4 µL precipitation-buffer containing sulfosalicyl acid. Then, 6 µL sample dilution buffer containing the internal standard norleucine (Nle, c: 1 nmol/µL) was added and samples were filled up to a final volume of 60 µL with sample dilution buffer. Thereafter, samples were mixed (Vortex) and centrifuged. The supernatants were passed through a centrifuge filter by centrifugation. The centrifugate was transferred into a sample vial and analyzed with the amino acid analyzer A200 using a physiologic program.

FIG. 4 and FIG. 5 show the effect of APIT at a single intravenous dose of 250 U/kg and 1000 U/kg to mice on plasma arginine or plasma lysine levels, respectively. A 4-fold increase of the APIT dose from 250 U/kg to 1000 U/kg results in an elongation of depletion of lysine or arginine from 3 h to 6 h post-dose.

FIGS. 6 and 7 show a direct comparison of the effect of unconjugated APIT and PEG-5000-APIT at a single intravenous dose of 250 U/kg. While unconjugated APIT mediates depletion of lysine (FIG. 6) and arginine (FIG. 7) only for 3 h post-dose, PEG-5000-APIT depletes both amino acids for at least 48 h post-dose.

Lysine and arginine plasma levels after single intravenous administration of different doses of PEG-5000-APIT to mice are shown in FIG. 8 and FIG. 9, respectively.

FIG. 8 demonstrates that a single intravenous dose of 11 Units/kg or 25 U/kg or 79 U/kg PEG-5000-APIT completely depletes plasma lysine levels in mice. A dose of 0.6 U/kg or 2 U/kg still mediates a complete depletion of Lysine in mice for 6 h, which is the effect of 1000 U/kg unconjugated APIT. FIG. 9 demonstrates that a single intravenous dose of 79 Units/kg PEG-5000-APIT completely depletes plasma arginine levels in mice. A dose of 25 U/kg or 11 U/kg mediates a complete depletion of arginine in mice for 24 h. A dose of 0.6 U/kg or 2 U/kg still mediates a complete depletion of arginine in mice for 6 h, which is the effect of 1000 U/kg unconjugated APIT.

Taken together, this unexpected findings demonstrated in FIGS. 8 and 9 mean that less than 0.1% PEG-5000-APIT relating to unconjugated APIT dose mediates equivalent effects on lysine and arginine levels in mammalians.

Example 5

Antitumor Efficacy of PEG-5000-APIT

The antitumor efficacy of PEG-5000-APIT was assessed in comparison to unconjugated APIT on A549 lung cancer cells by the MTT assay. The MTT assay is based upon the cleavage of the yellow tetrazolium salt MTT [3-(4,5-dimethylthiazol-2-yl)-2,5-diphenyl tetrazolium bromide] to purple formazan crystals by metabolically active cells. The tumor cells were seeded into 96-well culture plates and maintained in culture for 24 hours before adding the APIT or PEG-5000-APIT for another 96 h. After treatment, 20 µl of MTT labeling reagent were added to each well and plates were incubated at 37° C. for 4 h. Following MTT incubation, the cultures were incubated with DMSO and the spectrophotometric absorbance of the samples was detected by using a microtiter plate reader at a wavelength of 550 nm. The result was then plotted against the test substance concentration to obtain a dose-response curve. The test substance concentration that leads to 50% inhibition (IC50) of the metabolic activity was graphically determined and is shown for unconjugated APIT or PEG-5000-APIT in FIG. 10. Unexpectedly, the IC 50 of PEG-5000-APIT was lower (633 µU/mL) than the IC50 with unconjugated APIT (717 µU/mL) on A549 cells, indicating a higher antitumor effect of PEG-5000-APIT compared to that of unconjugated APIT.

REFERENCES

Butzke, D., Machuy, N., Thiede, B., Hurwitz, R., Goedert, S., & Rudel, T. (2004) Hydrogen peroxide produced by *Aplysia* ink toxin kills tumor cells independent of apoptosis via peroxiredoxin I sensitive pathways. *Cell Death. Differ.*, 11, 608-617.

Butzke, D. Hurwitz, R., Thiede, B., Goedert, S., and Rudel, T. (2005) Cloning and biochemical characterization of APIT, a new L-amino acid oxidase from *Aplysia punctata*. *Toxicon*, 46, 479-489.

Du, X. Y. & Clemetson, K. J. (2002) Snake venom L-amino acid oxidases. *Toxicon*, 40, 659-665.

Ponnudurai, G., Chung, M. C., & Tan, N. H. (1994) Purification and properties of the L-amino acid oxidase from Malayan pit viper (*Calloselasma rhodostoma*) venom. *Arch. Biochem. Biophys.*, 313, 373-378.

Jung, S. K., Mai, A., Iwamoto, M., Arizono, N., Fujimoto, D., Sakamaki, K., &Yonehara, S. (2000) Purification and cloning of an apoptosis-inducing protein derived from fish infected with Anisakis simplex, a causative nematode of human anisakiasis. *J. Immunol.,* 165, 1491-1497.

Ehara, T., Kitajima, S., Kanzawa, N., Tamiya, T., & Tsuchiya, T. (2002) Antimicrobial action of achacin is mediated by L-amino acid oxidase activity. *FEBS Lett.,* 531, 509-512.

Fang J, Sawa T, Akaike T, Maeda H. Tumor-targeted delivery of polyethylene glycol-conjugated D-amino acid oxidase for antitumor therapy via enzymatic generation of hydrogen peroxide. Cancer Res. 2002 Jun. 1; 62 (11):3138-43.

The invention claimed is:

1. A conjugate comprising an L-arginine/L-lysine oxidoreductase and at least one polyethylene glycol moiety wherein the L-arginine/L-lysine oxidoreductase has the sequence of SEQ ID NO: 8.

2. The conjugate of claim 1, wherein the at least one polyethylene glycol moiety has a weight average molecular weight of from about 1,000 Daltons to about 10,000 Daltons.

3. The conjugate of claim 1, wherein the at least one polyethylene glycol moiety is covalently coupled to the L-arginine/L-lysine oxidoreductase via a linking group.

4. The conjugate of claim 2, wherein the linking group is a succinimide group.

5. The conjugate of claim 2, wherein the at least one polyethylene glycol moiety is coupled via a lysine residue to the L-arginine/L-lysine oxidoreductase.

6. The conjugate of claim 1 comprising from 1 to about 30 polyethylene glycol moieties, preferably from 1 to about 10 polyethylene glycol moieties.

7. The conjugate of claim 1, wherein the L-arginine/L-lysine oxidoreductase is isolated from a natural source.

8. The conjugate of claim 1, wherein the L-arginine/L-lysine oxidoreductase is a recombinant arginine/lysine oxidoreductase.

9. The conjugate of claim 1, wherein the conjugate is active in the circulation of a subject for at least 6 hours.

10. The conjugate of claim 1, wherein the conjugate has an enzymatic activity which is a factor of at least 30 larger than the activity of an L-arginine/L-lysine oxidoreductase not carrying a polyethylene glycol moiety.

11. A pharmaceutical composition comprising the conjugate of claim 1 in combination with one or more pharmaceutically acceptable carriers, adjuvants, diluents and/or additives.

* * * * *

SEQUENCE LISTING

<160> NUMBER OF SEQ ID NOS: 8

<210> SEQ ID NO 1
<211> LENGTH: 1608
<212> TYPE: DNA
<213> ORGANISM: Aplysia punctata
<220> FEATURE:
<221> NAME/KEY: CDS
<222> LOCATION: (1)..(1608)

<400> SEQUENCE: 1

```
atg tcg tct gct gtg ctt ctc ctg gct tgt gcg ttg gtc atc tct gtc        48
Met Ser Ser Ala Val Leu Leu Leu Ala Cys Ala Leu Val Ile Ser Val
1               5                   10                  15 cac gcc gac ggt atc tgc aga aac aga cgt caa tgt aac aga gag gtg        96
His Ala Asp Gly Ile Cys Arg Asn Arg Arg Gln Cys Asn Arg Glu Val
                20                  25                  30 tgc ggt tct acc tac gat gtg gcc gtc gtg ggg gcg ggg cct ggg gga       144
Cys Gly Ser Thr Tyr Asp Val Ala Val Val Gly Ala Gly Pro Gly Gly
            35                  40                  45 gct aac tcc gcc tac atg ctg agg gac tcc ggc ctg gac atc gct gtg       192
Ala Asn Ser Ala Tyr Met Leu Arg Asp Ser Gly Leu Asp Ile Ala Val
        50                  55                  60 ttc gag tac tcg gac cga gtg ggc ggc cgg ctg ttc acc tac cag ctg       240
Phe Glu Tyr Ser Asp Arg Val Gly Gly Arg Leu Phe Thr Tyr Gln Leu
65                  70                  75                  80 ccc aac aca ccc gac gtt aac ctg gag att ggc ggc atg agg ttc atc       288
Pro Asn Thr Pro Asp Val Asn Leu Glu Ile Gly Gly Met Arg Phe Ile
                85                  90                  95 gaa ggc gcc atg cac agg ctc tgg agg gtc att tca gaa ctc ggc cta       336
Glu Gly Ala Met His Arg Leu Trp Arg Val Ile Ser Glu Leu Gly Leu
                100                 105                 110 acc ccc aag gtg ttc aag gaa ggt ttc ggc aag gag ggc aga caa aga       384
Thr Pro Lys Val Phe Lys Glu Gly Phe Gly Lys Glu Gly Arg Gln Arg
            115                 120                 125 ttt tac ctg cgg gga cag agc ctg acc aag aaa cag gtc aag agt ggg       432
Phe Tyr Leu Arg Gly Gln Ser Leu Thr Lys Lys Gln Val Lys Ser Gly
        130                 135                 140 gac gta ccc tat gac ctc agc ccg gag gag aaa gaa aac cag gga aat       480
Asp Val Pro Tyr Asp Leu Ser Pro Glu Glu Lys Glu Asn Gln Gly Asn
145                 150                 155                 160 ctg gtc gaa tac tac ctg gag aaa ctg aca ggt cta caa ctc aac ggc       528
Leu Val Glu Tyr Tyr Leu Glu Lys Leu Thr Gly Leu Gln Leu Asn Gly
                165                 170                 175 gag ccg ctc aaa cgt gag gtt gcg ctt aaa cta acc gtg ccg gac ggc       576
Glu Pro Leu Lys Arg Glu Val Ala Leu Lys Leu Thr Val Pro Asp Gly
                180                 185                 190 aga ttc ctc tat gac ctc tcg ttt gac gaa gcc atg gat ctg gtt gcc       624
Arg Phe Leu Tyr Asp Leu Ser Phe Asp Glu Ala Met Asp Leu Val Ala
            195                 200                 205 tcc cct gag ggc aaa gag ttc acc cga gac acg cac gtc ttc aca gga       672
Ser Pro Glu Gly Lys Glu Phe Thr Arg Asp Thr His Val Phe Thr Gly
        210                 215                 220 gag gtc acc ctg gac gcg tcg gct gtc tcc ctc ttc gac gac cac ctg       720
Glu Val Thr Leu Asp Ala Ser Ala Val Ser Leu Phe Asp Asp His Leu
```

```
                225                 230                 235                 240
gga gag gac tac tat ggc agt gag atc tac acc cta aag gaa gga ctg        768
Gly Glu Asp Tyr Tyr Gly Ser Glu Ile Tyr Thr Leu Lys Glu Gly Leu
                    245                 250                 255 tct tcc gtc cca caa ggg ctc cta cag gct ttt ctg gac gcc gca gac        816
Ser Ser Val Pro Gln Gly Leu Leu Gln Ala Phe Leu Asp Ala Ala Asp
                260                 265                 270 tcc aac gag ttc tat ccc aac agc cac ctg aag gcc ctg aga cgt aag        864
Ser Asn Glu Phe Tyr Pro Asn Ser His Leu Lys Ala Leu Arg Arg Lys
            275                 280                 285 acc aac ggt cag tat gtt ctt tac ttt gag ccc acc acc tcc aag gat        912
Thr Asn Gly Gln Tyr Val Leu Tyr Phe Glu Pro Thr Thr Ser Lys Asp
        290                 295                 300 gga caa acc aca atc aac tat ctg gaa ccc ctg cag gtt gtg tgt gca        960
Gly Gln Thr Thr Ile Asn Tyr Leu Glu Pro Leu Gln Val Val Cys Ala
305                 310                 315                 320 caa aga gtc atc ctg gcc atg ccg gta tac gct ctg aac caa cta gac       1008
Gln Arg Val Ile Leu Ala Met Pro Val Tyr Ala Leu Asn Gln Leu Asp
                    325                 330                 335 tgg aat cag ctc aga aat gac cga gcc acc caa gcg tac gct gcc gtt       1056
Trp Asn Gln Leu Arg Asn Asp Arg Ala Thr Gln Ala Tyr Ala Ala Val
                340                 345                 350 cgc ccg att cct gca agt aag gtg ttc atg tcc ttt gat cag ccc tgg       1104
Arg Pro Ile Pro Ala Ser Lys Val Phe Met Ser Phe Asp Gln Pro Trp
            355                 360                 365 tgg ttg gag aac gag agg aaa tcc tgg gtc acc aag tcg gac gcg ctt       1152
Trp Leu Glu Asn Glu Arg Lys Ser Trp Val Thr Lys Ser Asp Ala Leu
        370                 375                 380 ttc agc caa atg tac gac tgg cag aag tct gag gcg tcc gga gac tac       1200
Phe Ser Gln Met Tyr Asp Trp Gln Lys Ser Glu Ala Ser Gly Asp Tyr
385                 390                 395                 400 atc ctg atc gcc agc tac gcc gac ggc ctc aaa gcc cag tac ctg cgg       1248
Ile Leu Ile Ala Ser Tyr Ala Asp Gly Leu Lys Ala Gln Tyr Leu Arg
                    405                 410                 415 gag ctg aag aat cag gga gag gac atc cca ggc tct gac cca ggc tac       1296
Glu Leu Lys Asn Gln Gly Glu Asp Ile Pro Gly Ser Asp Pro Gly Tyr
                420                 425                 430 aac cag gtt acc gaa ccc ctc aag gac acc att ctt gac cac ctc act       1344
Asn Gln Val Thr Glu Pro Leu Lys Asp Thr Ile Leu Asp His Leu Thr
            435                 440                 445 gag gct tat ggc gtg gag cga gac tcg atc ccg gaa ccc gtg acc gcc       1392
Glu Ala Tyr Gly Val Glu Arg Asp Ser Ile Pro Glu Pro Val Thr Ala
        450                 455                 460 gct tcc cag ttc tgg aca gac tac ccg ttt ggc tgt gga tgg atc acc       1440
Ala Ser Gln Phe Trp Thr Asp Tyr Pro Phe Gly Cys Gly Trp Ile Thr
465                 470                 475                 480 tgg agg gcc ggc ttc cat ttc gat gac gtc atc agc acc atg cgt cgc       1488
Trp Arg Ala Gly Phe His Phe Asp Asp Val Ile Ser Thr Met Arg Arg
                    485                 490                 495 ccg tca ctg aaa gat gag gta tac gtg gtg gga gcc gac tac tcc tgg       1536
Pro Ser Leu Lys Asp Glu Val Tyr Val Val Gly Ala Asp Tyr Ser Trp
                500                 505                 510 gga ctt atc tcc tcc tgg ata gag ggc gct ctg gag acc tcg gaa aac       1584
Gly Leu Ile Ser Ser Trp Ile Glu Gly Ala Leu Glu Thr Ser Glu Asn
            515                 520                 525 gtc atc aac gac tac ttc ctc taa                                        1608
Val Ile Asn Asp Tyr Phe Leu
        530                 535

<210> SEQ ID NO 2
```

-continued

<211> LENGTH: 535
<212> TYPE: PRT
<213> ORGANISM: Aplysia punctata

<400> SEQUENCE: 2

```
Met Ser Ser Ala Val Leu Leu Ala Cys Ala Leu Val Ile Ser Val
1               5                   10                  15

His Ala Asp Gly Ile Cys Arg Asn Arg Gln Cys Asn Arg Glu Val
            20                  25                  30

Cys Gly Ser Thr Tyr Asp Val Ala Val Gly Ala Pro Gly Gly
        35                  40                  45

Ala Asn Ser Ala Tyr Met Leu Arg Asp Ser Gly Leu Asp Ile Ala Val
50                  55                  60

Phe Glu Tyr Ser Asp Arg Val Gly Gly Arg Leu Phe Thr Tyr Gln Leu
65                  70                  75                  80

Pro Asn Thr Pro Asp Val Asn Leu Glu Ile Gly Gly Met Arg Phe Ile
                85                  90                  95

Glu Gly Ala Met His Arg Leu Trp Arg Val Ile Ser Glu Leu Gly Leu
            100                 105                 110

Thr Pro Lys Val Phe Lys Glu Gly Phe Gly Lys Glu Gly Arg Gln Arg
            115                 120                 125

Phe Tyr Leu Arg Gly Gln Ser Leu Thr Lys Lys Gln Val Lys Ser Gly
        130                 135                 140

Asp Val Pro Tyr Asp Leu Ser Pro Glu Glu Lys Glu Asn Gln Gly Asn
145                 150                 155                 160

Leu Val Glu Tyr Tyr Leu Glu Lys Leu Thr Gly Leu Gln Leu Asn Gly
                165                 170                 175

Glu Pro Leu Lys Arg Glu Val Ala Leu Lys Leu Thr Val Pro Asp Gly
            180                 185                 190

Arg Phe Leu Tyr Asp Leu Ser Phe Asp Glu Ala Met Asp Leu Val Ala
        195                 200                 205

Ser Pro Glu Gly Lys Glu Phe Thr Arg Asp Thr His Val Phe Thr Gly
    210                 215                 220

Glu Val Thr Leu Asp Ala Ser Ala Val Ser Leu Phe Asp Asp His Leu
225                 230                 235                 240

Gly Glu Asp Tyr Tyr Gly Ser Glu Ile Tyr Thr Leu Lys Glu Gly Leu
                245                 250                 255

Ser Ser Val Pro Gln Gly Leu Leu Gln Ala Phe Leu Asp Ala Ala Asp
            260                 265                 270

Ser Asn Glu Phe Tyr Pro Asn Ser His Leu Lys Ala Leu Arg Arg Lys
        275                 280                 285

Thr Asn Gly Gln Tyr Val Leu Tyr Phe Glu Pro Thr Thr Ser Lys Asp
    290                 295                 300

Gly Gln Thr Thr Ile Asn Tyr Leu Glu Pro Leu Gln Val Val Cys Ala
305                 310                 315                 320

Gln Arg Val Ile Leu Ala Met Pro Val Tyr Ala Leu Asn Gln Leu Asp
                325                 330                 335

Trp Asn Gln Leu Arg Asn Asp Arg Ala Thr Gln Ala Tyr Ala Ala Val
            340                 345                 350

Arg Pro Ile Pro Ala Ser Lys Val Phe Met Ser Phe Asp Gln Pro Trp
        355                 360                 365

Trp Leu Glu Asn Glu Arg Lys Ser Trp Val Thr Lys Ser Asp Ala Leu
    370                 375                 380

Phe Ser Gln Met Tyr Asp Trp Gln Lys Ser Glu Ala Ser Gly Asp Tyr
385                 390                 395                 400
```

```
Ile Leu Ile Ala Ser Tyr Ala Asp Gly Leu Lys Ala Gln Tyr Leu Arg
                405                 410                 415
Glu Leu Lys Asn Gln Gly Glu Asp Ile Pro Gly Ser Asp Pro Gly Tyr
            420                 425                 430
Asn Gln Val Thr Glu Pro Leu Lys Asp Thr Ile Leu Asp His Leu Thr
        435                 440                 445
Glu Ala Tyr Gly Val Glu Arg Asp Ser Ile Pro Glu Pro Val Thr Ala
    450                 455                 460
Ala Ser Gln Phe Trp Thr Asp Tyr Pro Phe Gly Cys Gly Trp Ile Thr
465                 470                 475                 480
Trp Arg Ala Gly Phe His Phe Asp Asp Val Ile Ser Thr Met Arg Arg
                485                 490                 495
Pro Ser Leu Lys Asp Glu Val Tyr Val Val Gly Ala Asp Tyr Ser Trp
            500                 505                 510
Gly Leu Ile Ser Ser Trp Ile Glu Gly Ala Leu Glu Thr Ser Glu Asn
        515                 520                 525
Val Ile Asn Asp Tyr Phe Leu
        530                 535

<210> SEQ ID NO 3
<211> LENGTH: 1605
<212> TYPE: DNA
<213> ORGANISM: Aplysia punctata
<220> FEATURE:
<221> NAME/KEY: CDS
<222> LOCATION: (1)..(1605)

<400> SEQUENCE: 3 tcg tct gct gtg ctt ctc ctg gct tgt gcg ttg gtc atc tct gtc cac     48
Ser Ser Ala Val Leu Leu Leu Ala Cys Ala Leu Val Ile Ser Val His
1               5                   10                  15 gcc gac ggt gtc tgc aga aac aga cgt caa tgt aac aga gag gtg tgc     96
Ala Asp Gly Val Cys Arg Asn Arg Arg Gln Cys Asn Arg Glu Val Cys
            20                  25                  30 ggt tct acc tac gat gtg gcc gtc gtg ggg gcg ggg cct ggg gga gct    144
Gly Ser Thr Tyr Asp Val Ala Val Val Gly Ala Gly Pro Gly Gly Ala
        35                  40                  45 aac tcc gcc tac atg ctg agg gac tcc ggc ctg gac atc gct gtg ttc    192
Asn Ser Ala Tyr Met Leu Arg Asp Ser Gly Leu Asp Ile Ala Val Phe
    50                  55                  60 gag tac tca gac cga gtg ggc ggc cgg ctg ttc acc tac cag ctg ccc    240
Glu Tyr Ser Asp Arg Val Gly Gly Arg Leu Phe Thr Tyr Gln Leu Pro
65                  70                  75                  80 aac aca ccc gac gtt aat ctc gag att ggc ggc atg agg ttc atc gag    288
Asn Thr Pro Asp Val Asn Leu Glu Ile Gly Gly Met Arg Phe Ile Glu
                85                  90                  95 ggc gcc atg cac agg ctc tgg agg gtc att tca gaa ctc ggc cta acc    336
Gly Ala Met His Arg Leu Trp Arg Val Ile Ser Glu Leu Gly Leu Thr
            100                 105                 110 ccc aag gtg ttc aag gaa ggt ttc gga aag gag gga aga cag aga ttt    384
Pro Lys Val Phe Lys Glu Gly Phe Gly Lys Glu Gly Arg Gln Arg Phe
        115                 120                 125 tac ctg cgg gga cag agc ctg acc aag aaa cag gtc aag agt ggg gac    432
Tyr Leu Arg Gly Gln Ser Leu Thr Lys Lys Gln Val Lys Ser Gly Asp
    130                 135                 140 gta ccc tat gac ctc agc ccg gag gag aaa gaa aac cag gga aat ctg    480
Val Pro Tyr Asp Leu Ser Pro Glu Glu Lys Glu Asn Gln Gly Asn Leu
145                 150                 155                 160 gtc gaa tac tac ctg gag aaa ctg aca ggt cta caa ctc aat ggt gaa    528
```

-continued

```
            Val Glu Tyr Tyr Leu Glu Lys Leu Thr Gly Leu Gln Leu Asn Gly Glu
                            165                 170                 175 ccg ctc aaa cgt gag gtt gcg ctt aaa cta acc gtg ccg gac ggc aga       576
Pro Leu Lys Arg Glu Val Ala Leu Lys Leu Thr Val Pro Asp Gly Arg
                180                 185                 190 ttc ctc tat gac ctc tcg ttt gac gaa gcc atg gat ctg gtt gcc tcc       624
Phe Leu Tyr Asp Leu Ser Phe Asp Glu Ala Met Asp Leu Val Ala Ser
            195                 200                 205 cct gag ggc aaa gag ttc acc cga gac acg cac gtc ttc acc gga gag       672
Pro Glu Gly Lys Glu Phe Thr Arg Asp Thr His Val Phe Thr Gly Glu
        210                 215                 220 gtc acc ctg ggc gcg tcg gct gtc tcc ctc ttc gac gac cac ctg gga       720
Val Thr Leu Gly Ala Ser Ala Val Ser Leu Phe Asp Asp His Leu Gly
225                 230                 235                 240 gag gac tac tac ggc agt gag atc tac acc ctc aag gaa gga ctg tct       768
Glu Asp Tyr Tyr Gly Ser Glu Ile Tyr Thr Leu Lys Glu Gly Leu Ser
                245                 250                 255 tcc gtc cct caa ggg ctc cta cag gct ttt ctg gac gcc gca gac tcc       816
Ser Val Pro Gln Gly Leu Leu Gln Ala Phe Leu Asp Ala Ala Asp Ser
            260                 265                 270 aac gag ttc tat ccc aac agc cac ctg aag gcc ctg aga cgt aag acc       864
Asn Glu Phe Tyr Pro Asn Ser His Leu Lys Ala Leu Arg Arg Lys Thr
        275                 280                 285 aac ggt cag tat gtt ctt tac ttt gag ccc acc acc tcc aag gat gga       912
Asn Gly Gln Tyr Val Leu Tyr Phe Glu Pro Thr Thr Ser Lys Asp Gly
    290                 295                 300 caa acc aca atc aac tat ctg gaa ccc ctg cag gtt gtg tgt gca cag       960
Gln Thr Thr Ile Asn Tyr Leu Glu Pro Leu Gln Val Val Cys Ala Gln
305                 310                 315                 320 aga gtc att ctg gcc atg ccg gtc tac gct ctc aac cag ttg gat tgg      1008
Arg Val Ile Leu Ala Met Pro Val Tyr Ala Leu Asn Gln Leu Asp Trp
                325                 330                 335 aat cag ctc aga aat gac cga gcc acc caa gcg tac gct gcc gtg cgc      1056
Asn Gln Leu Arg Asn Asp Arg Ala Thr Gln Ala Tyr Ala Ala Val Arg
            340                 345                 350 ccg att cct gca agt aag gtg ttc atg acc ttt gat cag ccc tgg tgg      1104
Pro Ile Pro Ala Ser Lys Val Phe Met Thr Phe Asp Gln Pro Trp Trp
        355                 360                 365 ttg gag aac gag agg aaa tcc tgg gtc acc aag tcg gac gcg ctt ttc      1152
Leu Glu Asn Glu Arg Lys Ser Trp Val Thr Lys Ser Asp Ala Leu Phe
    370                 375                 380 agt caa atg tac gac tgg cag aag tct gag gcg tcc gga gac tac atc      1200
Ser Gln Met Tyr Asp Trp Gln Lys Ser Glu Ala Ser Gly Asp Tyr Ile
385                 390                 395                 400 ctg atc gcc agc tac gcc gac ggc ctc aaa gcc cag tac ctg cgg gag      1248
Leu Ile Ala Ser Tyr Ala Asp Gly Leu Lys Ala Gln Tyr Leu Arg Glu
                405                 410                 415 ctg aag aat cag gga gag gac atc cca ggc tct gac cca ggc tac aac      1296
Leu Lys Asn Gln Gly Glu Asp Ile Pro Gly Ser Asp Pro Gly Tyr Asn
            420                 425                 430 cag gtc acc gaa ccc ctc aag gac acc att ctt gac cac ctc act gag      1344
Gln Val Thr Glu Pro Leu Lys Asp Thr Ile Leu Asp His Leu Thr Glu
        435                 440                 445 gcc tat ggc gtg gag cga gac tcg atc cgg gaa ccc gtg acc gcc gct      1392
Ala Tyr Gly Val Glu Arg Asp Ser Ile Arg Glu Pro Val Thr Ala Ala
    450                 455                 460 tcc cag ttc tgg aca gac tac ccg ttt ggc tgt gga tgg atc acc tgg      1440
Ser Gln Phe Trp Thr Asp Tyr Pro Phe Gly Cys Gly Trp Ile Thr Trp
465                 470                 475                 480 agg gcc ggc ttc cat ttc gat gac gtc atc agc acc atg cgt cgc ccg      1488
```

```
                                                              -continued

Arg Ala Gly Phe His Phe Asp Asp Val Ile Ser Thr Met Arg Arg Pro
            485             490                 495 tca ctg aaa gat gag gtc tac gtg gtg gga gcc gat tac tcc tgg gga      1536
Ser Leu Lys Asp Glu Val Tyr Val Val Gly Ala Asp Tyr Ser Trp Gly
            500             505                 510 ctt atc tcc tcc tgg ata gag ggc gct ctg gag acc tca gaa aac gtc      1584
Leu Ile Ser Ser Trp Ile Glu Gly Ala Leu Glu Thr Ser Glu Asn Val
            515             520                 525 atc aac gac tac ttc ctc taa                                          1605
Ile Asn Asp Tyr Phe Leu
    530
```

<210> SEQ ID NO 4
<211> LENGTH: 534
<212> TYPE: PRT
<213> ORGANISM: Aplysia punctata

<400> SEQUENCE: 4

```
Ser Ser Ala Val Leu Leu Ala Cys Ala Leu Val Ile Ser Val His
1               5                   10                  15

Ala Asp Gly Val Cys Arg Asn Arg Arg Gln Cys Asn Arg Glu Val Cys
            20                  25                  30

Gly Ser Thr Tyr Asp Val Ala Val Gly Ala Gly Pro Gly Gly Ala
        35                  40                  45

Asn Ser Ala Tyr Met Leu Arg Asp Ser Gly Leu Asp Ile Ala Val Phe
    50                  55                  60

Glu Tyr Ser Asp Arg Val Gly Gly Arg Leu Phe Thr Tyr Gln Leu Pro
65                  70                  75                  80

Asn Thr Pro Asp Val Asn Leu Glu Ile Gly Gly Met Arg Phe Ile Glu
                85                  90                  95

Gly Ala Met His Arg Leu Trp Arg Val Ile Ser Glu Leu Gly Leu Thr
            100                 105                 110

Pro Lys Val Phe Lys Glu Gly Phe Gly Lys Glu Gly Arg Gln Arg Phe
        115                 120                 125

Tyr Leu Arg Gly Gln Ser Leu Thr Lys Lys Gln Val Lys Ser Gly Asp
    130                 135                 140

Val Pro Tyr Asp Leu Ser Pro Glu Glu Lys Glu Asn Gln Gly Asn Leu
145                 150                 155                 160

Val Glu Tyr Tyr Leu Glu Lys Leu Thr Gly Leu Gln Leu Asn Gly Glu
                165                 170                 175

Pro Leu Lys Arg Glu Val Ala Leu Lys Leu Thr Val Pro Asp Gly Arg
            180                 185                 190

Phe Leu Tyr Asp Leu Ser Phe Asp Glu Ala Met Asp Leu Val Ala Ser
        195                 200                 205

Pro Glu Gly Lys Glu Phe Thr Arg Asp Thr His Val Phe Thr Gly Glu
    210                 215                 220

Val Thr Leu Gly Ala Ser Ala Val Ser Leu Phe Asp Asp His Leu Gly
225                 230                 235                 240

Glu Asp Tyr Tyr Gly Ser Glu Ile Tyr Thr Leu Lys Glu Gly Leu Ser
                245                 250                 255

Ser Val Pro Gln Gly Leu Leu Gln Ala Phe Leu Asp Ala Ala Asp Ser
            260                 265                 270

Asn Glu Phe Tyr Pro Asn Ser His Leu Lys Ala Leu Arg Arg Lys Thr
        275                 280                 285

Asn Gly Gln Tyr Val Leu Tyr Phe Glu Pro Thr Thr Ser Lys Asp Gly
    290                 295                 300
```

```
Gln Thr Thr Ile Asn Tyr Leu Glu Pro Leu Gln Val Val Cys Ala Gln
305                 310                 315                 320

Arg Val Ile Leu Ala Met Pro Val Tyr Ala Leu Asn Gln Leu Asp Trp
            325                 330                 335

Asn Gln Leu Arg Asn Asp Arg Ala Thr Gln Ala Tyr Ala Ala Val Arg
        340                 345                 350

Pro Ile Pro Ala Ser Lys Val Phe Met Thr Phe Asp Gln Pro Trp Trp
    355                 360                 365

Leu Glu Asn Glu Arg Lys Ser Trp Val Thr Lys Ser Asp Ala Leu Phe
370                 375                 380

Ser Gln Met Tyr Asp Trp Gln Lys Ser Glu Ala Ser Gly Asp Tyr Ile
385                 390                 395                 400

Leu Ile Ala Ser Tyr Ala Asp Gly Leu Lys Ala Gln Tyr Leu Arg Glu
                405                 410                 415

Leu Lys Asn Gln Gly Glu Asp Ile Pro Gly Ser Asp Pro Gly Tyr Asn
            420                 425                 430

Gln Val Thr Glu Pro Leu Lys Asp Thr Ile Leu Asp His Leu Thr Glu
        435                 440                 445

Ala Tyr Gly Val Glu Arg Asp Ser Ile Arg Glu Pro Val Thr Ala Ala
    450                 455                 460

Ser Gln Phe Trp Thr Asp Tyr Pro Phe Gly Cys Gly Trp Ile Thr Trp
465                 470                 475                 480

Arg Ala Gly Phe His Phe Asp Val Ile Ser Thr Met Arg Arg Pro
                485                 490                 495

Ser Leu Lys Asp Glu Val Tyr Val Val Gly Ala Asp Tyr Ser Trp Gly
            500                 505                 510

Leu Ile Ser Ser Trp Ile Glu Gly Ala Leu Glu Thr Ser Glu Asn Val
        515                 520                 525

Ile Asn Asp Tyr Phe Leu
    530

<210> SEQ ID NO 5
<211> LENGTH: 1554
<212> TYPE: DNA
<213> ORGANISM: Aplysia punctata
<220> FEATURE:
<221> NAME/KEY: CDS
<222> LOCATION: (1)..(1554)

<400> SEQUENCE: 5 gac ggt atc tgc aga aac aga cgt caa tgt aac aga gag gtg tgc ggt      48
Asp Gly Ile Cys Arg Asn Arg Arg Gln Cys Asn Arg Glu Val Cys Gly
1               5                   10                  15 tct acc tac gat gtg gct gtc gtg ggg gcg ggg cct ggg gga gct aac      96
Ser Thr Tyr Asp Val Ala Val Val Gly Ala Gly Pro Gly Gly Ala Asn
            20                  25                  30 tcc gcc tac atg ctg agg gac tcc ggc ctg gac atc gct gtg ttc gag     144
Ser Ala Tyr Met Leu Arg Asp Ser Gly Leu Asp Ile Ala Val Phe Glu
        35                  40                  45 tac tca gac cga gtg ggc ggc cgg ctg ttc acc tac cag ctg ccc aac     192
Tyr Ser Asp Arg Val Gly Gly Arg Leu Phe Thr Tyr Gln Leu Pro Asn
    50                  55                  60 aca ccc gac gtt aat ctc gag att ggc ggc atg agg ttc atc gag ggc     240
Thr Pro Asp Val Asn Leu Glu Ile Gly Gly Met Arg Phe Ile Glu Gly
65                  70                  75                  80 gcc atg cac agg ctc tgg agg gtc att tca gaa ctc ggc cta acc ccc     288
Ala Met His Arg Leu Trp Arg Val Ile Ser Glu Leu Gly Leu Thr Pro
                85                  90                  95
```

```
aag gtg ttc aag gaa ggt ttc gga aag gag ggc aga cag aga ttt tac      336
Lys Val Phe Lys Glu Gly Phe Gly Lys Glu Gly Arg Gln Arg Phe Tyr
            100                 105                 110 ctg cgg gga cag agc ctg acc aag aaa cag gtc aag agt ggg gac gta      384
Leu Arg Gly Gln Ser Leu Thr Lys Lys Gln Val Lys Ser Gly Asp Val
        115                 120                 125 ccc tat gac ctc agc ccg gag gag aaa gaa aac cag gga aat ctg gtc      432
Pro Tyr Asp Leu Ser Pro Glu Glu Lys Glu Asn Gln Gly Asn Leu Val
    130                 135                 140 gaa tac tac ctg gag aaa ctg aca ggt cta aaa ctc aac ggc gga ccg      480
Glu Tyr Tyr Leu Glu Lys Leu Thr Gly Leu Lys Leu Asn Gly Gly Pro
145                 150                 155                 160 ctc aaa cgt gag gtt gcg ctt aaa cta acc gtg ccg gac ggc aga ttc      528
Leu Lys Arg Glu Val Ala Leu Lys Leu Thr Val Pro Asp Gly Arg Phe
                165                 170                 175 ctc tat gac ctc tcg ttt gac gaa gcc atg gac ctg gtt gcc tcc cct      576
Leu Tyr Asp Leu Ser Phe Asp Glu Ala Met Asp Leu Val Ala Ser Pro
            180                 185                 190 gag ggc aaa gag ttc acc cga gac acg cac gtg ttc acc gga gaa gtc      624
Glu Gly Lys Glu Phe Thr Arg Asp Thr His Val Phe Thr Gly Glu Val
        195                 200                 205 acc ctg gac gcg tcg gct gtc tcc ctc ttc gac gac cac ctg gga gag      672
Thr Leu Asp Ala Ser Ala Val Ser Leu Phe Asp Asp His Leu Gly Glu
    210                 215                 220 gac tac tat ggc agt gag atc tac acc cta aag gaa gga ctg tct tcc      720
Asp Tyr Tyr Gly Ser Glu Ile Tyr Thr Leu Lys Glu Gly Leu Ser Ser
225                 230                 235                 240 gtc cca caa ggg ctc cta cag act ttt ctg gac gcc gca gac tcc aac      768
Val Pro Gln Gly Leu Leu Gln Thr Phe Leu Asp Ala Ala Asp Ser Asn
                245                 250                 255 gag ttc tat ccc aac agc cac ctg aag gcc ctg aga cgt aag acc aac      816
Glu Phe Tyr Pro Asn Ser His Leu Lys Ala Leu Arg Arg Lys Thr Asn
            260                 265                 270 ggt cag tat gtt ctt tac ttt gag ccc acc acc tcc aag gat gga caa      864
Gly Gln Tyr Val Leu Tyr Phe Glu Pro Thr Thr Ser Lys Asp Gly Gln
        275                 280                 285 acc aca atc aac tat ctg gaa ccc ctg cag gtt gtg tgt gca cag aga      912
Thr Thr Ile Asn Tyr Leu Glu Pro Leu Gln Val Val Cys Ala Gln Arg
    290                 295                 300 gtc atc ctg gcc atg ccg gtc tac gct ctc aac caa ctg gac tgg aat      960
Val Ile Leu Ala Met Pro Val Tyr Ala Leu Asn Gln Leu Asp Trp Asn
305                 310                 315                 320 cag ctc aga aat gac cga gcc acc caa gcg tac gct gcc gtg cgc ccg     1008
Gln Leu Arg Asn Asp Arg Ala Thr Gln Ala Tyr Ala Ala Val Arg Pro
                325                 330                 335 att cct gca agt aaa gtg ttc atg acc ttt gat cag ccc tgg tgg ttg     1056
Ile Pro Ala Ser Lys Val Phe Met Thr Phe Asp Gln Pro Trp Trp Leu
            340                 345                 350 gag aac gag agg aaa tcc tgg gtc acc aag tcg gac gcg ctt ttc agc     1104
Glu Asn Glu Arg Lys Ser Trp Val Thr Lys Ser Asp Ala Leu Phe Ser
        355                 360                 365 caa atg tac gac tgg cag aag tct gag gcg tcc gga gac tac atc ctg     1152
Gln Met Tyr Asp Trp Gln Lys Ser Glu Ala Ser Gly Asp Tyr Ile Leu
    370                 375                 380 atc gcc agc tac gcc gac ggc ctc aaa gcc cag tac ctg cgg gag ctg     1200
Ile Ala Ser Tyr Ala Asp Gly Leu Lys Ala Gln Tyr Leu Arg Glu Leu
385                 390                 395                 400 aag aat cag gga gag gac atc cca ggc tct gac cca ggc tac aac cag     1248
Lys Asn Gln Gly Glu Asp Ile Pro Gly Ser Asp Pro Gly Tyr Asn Gln
                405                 410                 415
```

```
gtc acc gaa ccc ctc aag gac acc att ctt gac cac ctc act gag gct    1296
Val Thr Glu Pro Leu Lys Asp Thr Ile Leu Asp His Leu Thr Glu Ala
            420                 425                 430 tat ggc gtg gaa cga gac tcg atc ccg gaa ccc gtg acc gcc gct tcc    1344
Tyr Gly Val Glu Arg Asp Ser Ile Pro Glu Pro Val Thr Ala Ala Ser
        435                 440                 445 cag ttc tgg acc gac tac ccg ttc ggc tgt gga tgg atc acc tgg agg    1392
Gln Phe Trp Thr Asp Tyr Pro Phe Gly Cys Gly Trp Ile Thr Trp Arg
    450                 455                 460 gca ggc ttc cat ttt gat gac gtc atc agc acc atg cgt cgc ccg tca    1440
Ala Gly Phe His Phe Asp Asp Val Ile Ser Thr Met Arg Arg Pro Ser
465                 470                 475                 480 ctg aaa gat gag gtc tac gtg gtg gga gcc gat tac tcc tgg gga ctt    1488
Leu Lys Asp Glu Val Tyr Val Val Gly Ala Asp Tyr Ser Trp Gly Leu
                485                 490                 495 atc tcc tcc tgg ata gag ggc gct ctg gag acc tcg gaa aac gtc atc    1536
Ile Ser Ser Trp Ile Glu Gly Ala Leu Glu Thr Ser Glu Asn Val Ile
            500                 505                 510 aac gac tac ttc ctc taa                                            1554
Asn Asp Tyr Phe Leu
        515

<210> SEQ ID NO 6
<211> LENGTH: 517
<212> TYPE: PRT
<213> ORGANISM: Aplysia punctata

<400> SEQUENCE: 6

Asp Gly Ile Cys Arg Asn Arg Arg Gln Cys Asn Arg Glu Val Cys Gly
1               5                   10                  15

Ser Thr Tyr Asp Val Ala Val Val Gly Ala Gly Pro Gly Gly Ala Asn
            20                  25                  30

Ser Ala Tyr Met Leu Arg Asp Ser Gly Leu Asp Ile Ala Val Phe Glu
        35                  40                  45

Tyr Ser Asp Arg Val Gly Gly Arg Leu Phe Thr Tyr Gln Leu Pro Asn
    50                  55                  60

Thr Pro Asp Val Asn Leu Glu Ile Gly Gly Met Arg Phe Ile Glu Gly
65                  70                  75                  80

Ala Met His Arg Leu Trp Arg Val Ile Ser Glu Leu Gly Leu Thr Pro
                85                  90                  95

Lys Val Phe Lys Glu Gly Phe Gly Lys Glu Gly Arg Gln Arg Phe Tyr
            100                 105                 110

Leu Arg Gly Gln Ser Leu Thr Lys Lys Gln Val Lys Ser Gly Asp Val
        115                 120                 125

Pro Tyr Asp Leu Ser Pro Glu Glu Lys Glu Asn Gln Gly Asn Leu Val
    130                 135                 140

Glu Tyr Tyr Leu Glu Lys Leu Thr Gly Leu Lys Leu Asn Gly Pro
145                 150                 155                 160

Leu Lys Arg Glu Val Ala Leu Lys Leu Thr Val Pro Asp Gly Arg Phe
                165                 170                 175

Leu Tyr Asp Leu Ser Phe Asp Glu Ala Met Asp Leu Val Ala Ser Pro
            180                 185                 190

Glu Gly Lys Glu Phe Thr Arg Asp Thr His Val Phe Thr Gly Glu Val
        195                 200                 205

Thr Leu Asp Ala Ser Ala Val Ser Leu Phe Asp Asp His Leu Gly Glu
    210                 215                 220

Asp Tyr Tyr Gly Ser Glu Ile Tyr Thr Leu Lys Glu Gly Leu Ser Ser
225                 230                 235                 240
```

```
Val Pro Gln Gly Leu Leu Gln Thr Phe Leu Asp Ala Ala Asp Ser Asn
            245                 250                 255

Glu Phe Tyr Pro Asn Ser His Leu Lys Ala Leu Arg Arg Lys Thr Asn
                260                 265                 270

Gly Gln Tyr Val Leu Tyr Phe Glu Pro Thr Thr Ser Lys Asp Gly Gln
            275                 280                 285

Thr Thr Ile Asn Tyr Leu Glu Pro Leu Gln Val Val Cys Ala Gln Arg
290                 295                 300

Val Ile Leu Ala Met Pro Val Tyr Ala Leu Asn Gln Leu Asp Trp Asn
305                 310                 315                 320

Gln Leu Arg Asn Asp Arg Ala Thr Gln Ala Tyr Ala Ala Val Arg Pro
                325                 330                 335

Ile Pro Ala Ser Lys Val Phe Met Thr Phe Asp Gln Pro Trp Trp Leu
            340                 345                 350

Glu Asn Glu Arg Lys Ser Trp Val Thr Lys Ser Asp Ala Leu Phe Ser
                355                 360                 365

Gln Met Tyr Asp Trp Gln Lys Ser Glu Ala Ser Gly Asp Tyr Ile Leu
            370                 375                 380

Ile Ala Ser Tyr Ala Asp Gly Leu Lys Ala Gln Tyr Leu Arg Glu Leu
385                 390                 395                 400

Lys Asn Gln Gly Glu Asp Ile Pro Gly Ser Asp Pro Gly Tyr Asn Gln
                405                 410                 415

Val Thr Glu Pro Leu Lys Asp Thr Ile Leu Asp His Leu Thr Glu Ala
            420                 425                 430

Tyr Gly Val Glu Arg Asp Ser Ile Pro Glu Pro Val Thr Ala Ala Ser
            435                 440                 445

Gln Phe Trp Thr Asp Tyr Pro Phe Gly Cys Gly Trp Ile Thr Trp Arg
            450                 455                 460

Ala Gly Phe His Phe Asp Asp Val Ile Ser Thr Met Arg Arg Pro Ser
465                 470                 475                 480

Leu Lys Asp Glu Val Tyr Val Gly Ala Asp Tyr Ser Trp Gly Leu
                485                 490                 495

Ile Ser Ser Trp Ile Glu Gly Ala Leu Glu Thr Ser Glu Asn Val Ile
            500                 505                 510

Asn Asp Tyr Phe Leu
            515

<210> SEQ ID NO 7
<211> LENGTH: 1554
<212> TYPE: DNA
<213> ORGANISM: Aplysia punctata
<220> FEATURE:
<221> NAME/KEY: CDS
<222> LOCATION: (1)..(1554)

<400> SEQUENCE: 7 atg gac ggt gtc agc aga aac aga cgt caa tgt aac aga gag gtg tgc      48
Met Asp Gly Val Ser Arg Asn Arg Arg Gln Cys Asn Arg Glu Val Cys
1               5                   10                  15 ggt tct acc tac gat gtg gcc gtc gtg ggg gcg ggg cct ggg gga gct      96
Gly Ser Thr Tyr Asp Val Ala Val Val Gly Ala Gly Pro Gly Gly Ala
                20                  25                  30 aac tcc gcc tac atg ctg agg gac tcc ggc ctg gac atc gct gtg ttc     144
Asn Ser Ala Tyr Met Leu Arg Asp Ser Gly Leu Asp Ile Ala Val Phe
            35                  40                  45 gag tac tca gac cga gtg ggc ggc cgg ctg ttc acc tac cag ctg ccc     192
Glu Tyr Ser Asp Arg Val Gly Gly Arg Leu Phe Thr Tyr Gln Leu Pro
```

```
              50                  55                  60
aac aca ccc gac gtt aac ctg gag att gga ggc atg agg ttc atc gaa       240
Asn Thr Pro Asp Val Asn Leu Glu Ile Gly Gly Met Arg Phe Ile Glu
 65                  70                  75                  80 ggc gcc atg cac agg ctc tgg agg gtc att tca gaa ctc ggc cta acc       288
Gly Ala Met His Arg Leu Trp Arg Val Ile Ser Glu Leu Gly Leu Thr
                 85                  90                  95 ccc aag gtg ttc aag gaa ggt ttc ggc aag gag ggc aga caa aga ttc       336
Pro Lys Val Phe Lys Glu Gly Phe Gly Lys Glu Gly Arg Gln Arg Phe
            100                 105                 110 tac ctg cgg gga cag agc ctg acc aag aaa cag gtc aag agt ggg gac       384
Tyr Leu Arg Gly Gln Ser Leu Thr Lys Lys Gln Val Lys Ser Gly Asp
                115                 120                 125 gta ccc tat gac ctc agc ccg gag gag aaa gaa aac cag gga aat ctg       432
Val Pro Tyr Asp Leu Ser Pro Glu Glu Lys Glu Asn Gln Gly Asn Leu
    130                 135                 140 gtc gaa tac tac ctg gag aaa ctg aca ggt cta caa ctc aac ggc gag       480
Val Glu Tyr Tyr Leu Glu Lys Leu Thr Gly Leu Gln Leu Asn Gly Glu
145                 150                 155                 160 ccg ctc aaa cgt gag gtt gcg ctt aaa cta acc gtg ccg gac ggc aga       528
Pro Leu Lys Arg Glu Val Ala Leu Lys Leu Thr Val Pro Asp Gly Arg
                165                 170                 175 ttc ctc tat gac ctc tcg ttt gac gaa gcc atg gat ctg gtt gcc tcc       576
Phe Leu Tyr Asp Leu Ser Phe Asp Glu Ala Met Asp Leu Val Ala Ser
            180                 185                 190 cct gag ggc aaa gag ttc acc cga gac acg cac gtc ttc aca gga gag       624
Pro Glu Gly Lys Glu Phe Thr Arg Asp Thr His Val Phe Thr Gly Glu
                195                 200                 205 gtc acc ctg gac gcg tcg gct gtc tcc ctc ttc gac gac cac ctg gga       672
Val Thr Leu Asp Ala Ser Ala Val Ser Leu Phe Asp Asp His Leu Gly
    210                 215                 220 gag gac tac tat ggc agt gag atc tac acc cta aag gaa gga ctg tct       720
Glu Asp Tyr Tyr Gly Ser Glu Ile Tyr Thr Leu Lys Glu Gly Leu Ser
225                 230                 235                 240 tcc gtc cca caa ggg ctc cta cag gct ttt ctg gac gcc gca gac tcc       768
Ser Val Pro Gln Gly Leu Leu Gln Ala Phe Leu Asp Ala Ala Asp Ser
                245                 250                 255 aac gag ttc tat ccc aac agc cac ctg aag gcc ctg aga cgt aag acc       816
Asn Glu Phe Tyr Pro Asn Ser His Leu Lys Ala Leu Arg Arg Lys Thr
            260                 265                 270 aac ggt cag tat gtt ctt tac ttt gag ccc acc acc tcc aag gat gga       864
Asn Gly Gln Tyr Val Leu Tyr Phe Glu Pro Thr Thr Ser Lys Asp Gly
                275                 280                 285 caa acc aca atc aac tat ctg gaa ccc ctg cag gtt gtg tgt gca cag       912
Gln Thr Thr Ile Asn Tyr Leu Glu Pro Leu Gln Val Val Cys Ala Gln
    290                 295                 300 aga gtc atc ctg gcc atg ccg gta tac gct ctg aac caa cta gac tgg       960
Arg Val Ile Leu Ala Met Pro Val Tyr Ala Leu Asn Gln Leu Asp Trp
305                 310                 315                 320 aat cag ctc aga aat gac cga gcc acc caa gcg tac gct gcc gtt cgc      1008
Asn Gln Leu Arg Asn Asp Arg Ala Thr Gln Ala Tyr Ala Ala Val Arg
                325                 330                 335 ccg att cct gca agt aag gtg ttc atg acc ttt gat cag ccc tgg tgg      1056
Pro Ile Pro Ala Ser Lys Val Phe Met Thr Phe Asp Gln Pro Trp Trp
            340                 345                 350 ttg gag aac gag agg aaa tcc tgg gtc acc aag tcg gac gcg ctt ttc      1104
Leu Glu Asn Glu Arg Lys Ser Trp Val Thr Lys Ser Asp Ala Leu Phe
                355                 360                 365 agc caa atg tac gac tgg cag aag tct gag gcg tcc gga gac tac atc      1152
Ser Gln Met Tyr Asp Trp Gln Lys Ser Glu Ala Ser Gly Asp Tyr Ile
```

```
            370                 375                 380
ctg atc gcc agc tac gcc gac ggc ctc aaa gcc cag tac ctg cgg gag    1200
Leu Ile Ala Ser Tyr Ala Asp Gly Leu Lys Ala Gln Tyr Leu Arg Glu
385                 390                 395                 400 ctg aag aat cag gga gag gac atc cca ggc tct gac cca ggc tac aac    1248
Leu Lys Asn Gln Gly Glu Asp Ile Pro Gly Ser Asp Pro Gly Tyr Asn
            405                 410                 415 cag gtc acc gaa ccc ctc aag gac acc att ctt gac cac ctc act gag    1296
Gln Val Thr Glu Pro Leu Lys Asp Thr Ile Leu Asp His Leu Thr Glu
        420                 425                 430 gct tat ggc gtg gaa cga gac tcg atc ccg gaa ccc gtg acc gcc gct    1344
Ala Tyr Gly Val Glu Arg Asp Ser Ile Pro Glu Pro Val Thr Ala Ala
        435                 440                 445 tcc cag ttc tgg aca gac tac ccg ttt ggc tgt gga tgg atc acc tgg    1392
Ser Gln Phe Trp Thr Asp Tyr Pro Phe Gly Cys Gly Trp Ile Thr Trp
450                 455                 460 agg gcc ggc ttc cat ttc gat gac gtc atc agc acc atg cgt cgc ccg    1440
Arg Ala Gly Phe His Phe Asp Asp Val Ile Ser Thr Met Arg Arg Pro
465                 470                 475                 480 tca ctg aaa gat gag gta tac gtg gtg gga gcc gac tac tcc tgg gga    1488
Ser Leu Lys Asp Glu Val Tyr Val Val Gly Ala Asp Tyr Ser Trp Gly
                485                 490                 495 ctt atc tcc tcc tgg ata gag ggc gct ctt gag acc tcg gaa aac gtc    1536
Leu Ile Ser Ser Trp Ile Glu Gly Ala Leu Glu Thr Ser Glu Asn Val
            500                 505                 510 atc aac gac tac ttc ctc                                            1554
Ile Asn Asp Tyr Phe Leu
            515

<210> SEQ ID NO 8
<211> LENGTH: 518
<212> TYPE: PRT
<213> ORGANISM: Aplysia punctata

<400> SEQUENCE: 8

Met Asp Gly Val Ser Arg Asn Arg Arg Gln Cys Asn Arg Glu Val Cys
1               5                   10                  15

Gly Ser Thr Tyr Asp Val Ala Val Gly Ala Gly Pro Gly Gly Ala
            20                  25                  30

Asn Ser Ala Tyr Met Leu Arg Asp Ser Gly Leu Asp Ile Ala Val Phe
        35                  40                  45

Glu Tyr Ser Asp Arg Val Gly Gly Arg Leu Phe Thr Tyr Gln Leu Pro
    50                  55                  60

Asn Thr Pro Asp Val Asn Leu Glu Ile Gly Gly Met Arg Phe Ile Glu
65                  70                  75                  80

Gly Ala Met His Arg Leu Trp Arg Val Ile Ser Glu Leu Gly Leu Thr
                85                  90                  95

Pro Lys Val Phe Lys Glu Gly Phe Gly Lys Glu Gly Arg Gln Arg Phe
            100                 105                 110

Tyr Leu Arg Gly Gln Ser Leu Thr Lys Lys Gln Val Lys Ser Gly Asp
        115                 120                 125

Val Pro Tyr Asp Leu Ser Pro Glu Glu Lys Glu Asn Gln Gly Asn Leu
    130                 135                 140

Val Glu Tyr Tyr Leu Glu Lys Leu Thr Gly Leu Gln Leu Asn Gly Glu
145                 150                 155                 160

Pro Leu Lys Arg Glu Val Ala Leu Lys Leu Thr Val Pro Asp Gly Arg
                165                 170                 175

Phe Leu Tyr Asp Leu Ser Phe Asp Glu Ala Met Asp Leu Val Ala Ser
```

-continued

```
                180                 185                 190
Pro Glu Gly Lys Glu Phe Thr Arg Asp Thr His Val Phe Thr Gly Glu
                195                 200                 205
Val Thr Leu Asp Ala Ser Ala Val Ser Leu Phe Asp Asp His Leu Gly
    210                 215                 220
Glu Asp Tyr Tyr Gly Ser Glu Ile Tyr Thr Leu Lys Glu Gly Leu Ser
225                 230                 235                 240
Ser Val Pro Gln Gly Leu Leu Gln Ala Phe Leu Asp Ala Ala Asp Ser
                245                 250                 255
Asn Glu Phe Tyr Pro Asn Ser His Leu Lys Ala Leu Arg Arg Lys Thr
                260                 265                 270
Asn Gly Gln Tyr Val Leu Tyr Phe Glu Pro Thr Thr Ser Lys Asp Gly
                275                 280                 285
Gln Thr Thr Ile Asn Tyr Leu Glu Pro Leu Gln Val Val Cys Ala Gln
                290                 295                 300
Arg Val Ile Leu Ala Met Pro Val Tyr Ala Leu Asn Gln Leu Asp Trp
305                 310                 315                 320
Asn Gln Leu Arg Asn Asp Arg Ala Thr Gln Ala Tyr Ala Ala Val Arg
                325                 330                 335
Pro Ile Pro Ala Ser Lys Val Phe Met Thr Phe Asp Gln Pro Trp Trp
                340                 345                 350
Leu Glu Asn Glu Arg Lys Ser Trp Val Thr Lys Ser Asp Ala Leu Phe
                355                 360                 365
Ser Gln Met Tyr Asp Trp Gln Lys Ser Glu Ala Ser Gly Asp Tyr Ile
                370                 375                 380
Leu Ile Ala Ser Tyr Ala Asp Gly Leu Lys Ala Gln Tyr Leu Arg Glu
385                 390                 395                 400
Leu Lys Asn Gln Gly Glu Asp Ile Pro Gly Ser Asp Pro Gly Tyr Asn
                405                 410                 415
Gln Val Thr Glu Pro Leu Lys Asp Thr Ile Leu Asp His Leu Thr Glu
                420                 425                 430
Ala Tyr Gly Val Glu Arg Asp Ser Ile Pro Glu Pro Val Thr Ala Ala
                435                 440                 445
Ser Gln Phe Trp Thr Asp Tyr Pro Phe Gly Cys Gly Trp Ile Thr Trp
                450                 455                 460
Arg Ala Gly Phe His Phe Asp Asp Val Ile Ser Thr Met Arg Arg Pro
465                 470                 475                 480
Ser Leu Lys Asp Glu Val Tyr Val Val Gly Ala Asp Tyr Ser Trp Gly
                485                 490                 495
Leu Ile Ser Ser Trp Ile Glu Gly Ala Leu Glu Thr Ser Glu Asn Val
                500                 505                 510
Ile Asn Asp Tyr Phe Leu
                515
```